(12) United States Patent
Chan et al.

(10) Patent No.: US 11,172,909 B2
(45) Date of Patent: Nov. 16, 2021

(54) SENSOR FUSION TO VALIDATE SOUND-PRODUCING BEHAVIORS

(71) Applicant: BIOINTELLISENSE, INC., Golden, CO (US)

(72) Inventors: Eduardo Chan, San Jose, CA (US);
James Mault, Evergreen, CO (US);
David Wang, Palo Alto, CA (US);
Henry Leung, Sunnyvale, CA (US);
Sam Jones, Millbrae, CA (US); Mark Ross, San Carlos, CA (US)

(73) Assignee: BIOINTELLISENSE, INC., Golden, CO (US)

( * ) Notice: Subject to any disclaimer, the term of this patent is extended or adjusted under 35 U.S.C. 154(b) by 441 days.

(21) Appl. No.: 16/118,242

(22) Filed: Aug. 30, 2018

(65) Prior Publication Data
US 2020/0069281 A1 Mar. 5, 2020

(51) Int. Cl.
*A61B 7/04* (2006.01)
*G10L 25/66* (2013.01)
(Continued)

(52) U.S. Cl.
CPC ............ *A61B 7/04* (2013.01); *A61B 5/02055* (2013.01); *A61B 5/4809* (2013.01); *A61B 5/681* (2013.01); *A61B 5/7221* (2013.01); *A61B 5/7264* (2013.01); *A61B 5/7278* (2013.01); *A61B 5/7282* (2013.01); *A61B 7/003* (2013.01); *A61B 7/008* (2013.01); *G10L 25/66* (2013.01); *H04R 29/00* (2013.01); *A61B 5/0261* (2013.01); *A61B 5/0531* (2013.01); *A61B 5/0823* (2013.01);
(Continued)

(58) Field of Classification Search
CPC ............................. A61B 7/04; A61B 5/02055
USPC .......................................................... 600/301
See application file for complete search history.

(56) References Cited

U.S. PATENT DOCUMENTS

| 7,559,903 B2 | 7/2009 | Moussavi et al. |
| 2006/0064037 A1* | 3/2006 | Shalon .................. G16H 20/60 600/586 |

(Continued)

OTHER PUBLICATIONS

Michael G. Levitzky, Using the pathaphysiology of obstructive sleep apnea to teach cardiopulmonary integration, American Physiological Society, Sep. 1, 2008, http://advan.physiology.org/content/32/3/196.
Lorenzo Ferranti, Rita Laureanti, Atrial Fibrillation detection in PPG signal recorded through a wristband device, Politesi Digital Archive, Dec. 18, 2015, http://hdl.handle.net/10589/115204.
(Continued)

*Primary Examiner* — Nadia A Mahmood
(74) *Attorney, Agent, or Firm* — Maschoff Brennan

(57) ABSTRACT

A method to measure sound-producing behaviors of a subject with a power- and bandwidth-limited electronic device that includes a processor includes measuring, by a microphone communicatively coupled to the processor, sound in a vicinity of the subject to generate an audio data signal that represents the sound. The method also includes measuring, by at least one second sensor communicatively coupled to the processor, at least one parameter other than sound to generate at least a second data signal that represents the at least one parameter other than sound. The method also includes detecting one or more sound-producing behaviors of the subject based on: both the audio data signal and the second data signal; or information derived from both the audio data signal and the second data signal.

7 Claims, 13 Drawing Sheets

(51) Int. Cl.
| | |
|---|---|
| *A61B 5/00* | (2006.01) |
| *A61B 5/0205* | (2006.01) |
| *A61B 7/00* | (2006.01) |
| *H04R 29/00* | (2006.01) |
| *A61B 5/08* | (2006.01) |
| *A61B 5/026* | (2006.01) |
| *A61B 5/0531* | (2021.01) |
| *A61B 5/113* | (2006.01) |
| *A61B 5/1455* | (2006.01) |
| *A61B 5/318* | (2021.01) |

(52) U.S. Cl.
CPC ........... *A61B 5/113* (2013.01); *A61B 5/14551* (2013.01); *A61B 5/318* (2021.01); *A61B 2562/0204* (2013.01); *A61B 2562/0219* (2013.01)

(56) References Cited

U.S. PATENT DOCUMENTS

| | | |
|---|---|---|
| 2008/0275349 A1 | 11/2008 | Halperin et al. |
| 2012/0071741 A1 | 3/2012 | Moussavi et al. |
| 2015/0018693 A1 | 1/2015 | Mestha et al. |
| 2016/0235344 A1 | 8/2016 | Auerbach |

OTHER PUBLICATIONS

Xiao Sun, Zongquing Lu, Wenjie Hu, Guohong Cao, SymDetector: Detecting Sound-Related Respiratory Symptoms Using Smartphones, UBICOMP '15, Sep. 2015.
International Search Report and Written Opinion issued in corresponding PCT Application No. PCT/US2019/048928, dated Nov. 12, 2019.

\* cited by examiner

SENSOR FUSION TO VALIDATE SOUND-PRODUCING BEHAVIORS

FIELD

Some embodiments described herein generally relate to sensor fusion to validate sound-producing behaviors.

BACKGROUND

Unless otherwise indicated herein, the materials described herein are not prior art to the claims in the present application and are not admitted to be prior art by inclusion in this section.

Sound-related behaviors such as sneezing, coughing, vomiting, shouting (e.g., tied to mood or rage) may be useful to measure in health-related research. For example, measuring sneezing, coughing, vomiting, shouting may be useful in researching the intended effects and/or side effects of a given medication. Such behaviors have been self-reported in the past, but self-reporting may be cumbersome to subjects, may be inefficient, and/or may be inaccurate.

Some methods have been proposed to automatically measure, e.g., sneezing and/or coughing. Such methods often have to be implemented in noise-free or at least low-noise environments such as in a clinical setting. Such constraints may make such methods expensive and/or difficult to deploy on a large scale.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Some example embodiments described herein generally relate to sensor fusion to validate sound-producing behaviors of a subject.

In an example embodiment, a method to measure sound-producing behaviors of a subject with a power- and bandwidth-limited electronic device that includes a processor includes measuring, by a microphone communicatively coupled to the processor, sound in a vicinity of the subject to generate an audio data signal that represents the sound. The method also includes measuring, by at least one second sensor communicatively coupled to the processor, at least one parameter other than sound to generate at least a second data signal that represents the at least one parameter other than sound. The method also includes detecting one or more sound-producing behaviors of the subject based on: both the audio data signal and the second data signal; or information derived from both the audio data signal and the second data signal.

In another example embodiment, a power- and bandwidth-limited system to measure sound-producing behaviors of a subject, includes a processor, a microphone, at least one second sensor, and a non-transitory computer-readable medium. The microphone is communicatively coupled to the processor and is configured to generate an audio data signal that represents sound in a vicinity of the subject. The at least one second sensor is communicatively coupled to the processor and is configured to generate at least a second data signal that represents at least one parameter other than sound. The non-transitory computer-readable medium is communicatively coupled to the processor and has computer-executable instructions stored thereon that are executable by the processor to perform or control performance of operations. The operations include receiving the audio data signal from the microphone. The operations also include receiving the second data signal from the at least one second sensor. The operations also include detecting one or more sound-producing behaviors of the subject based on: both the audio data signal and the second data signal; or information derived from both the audio data signal and the second data signal.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Figure 1:
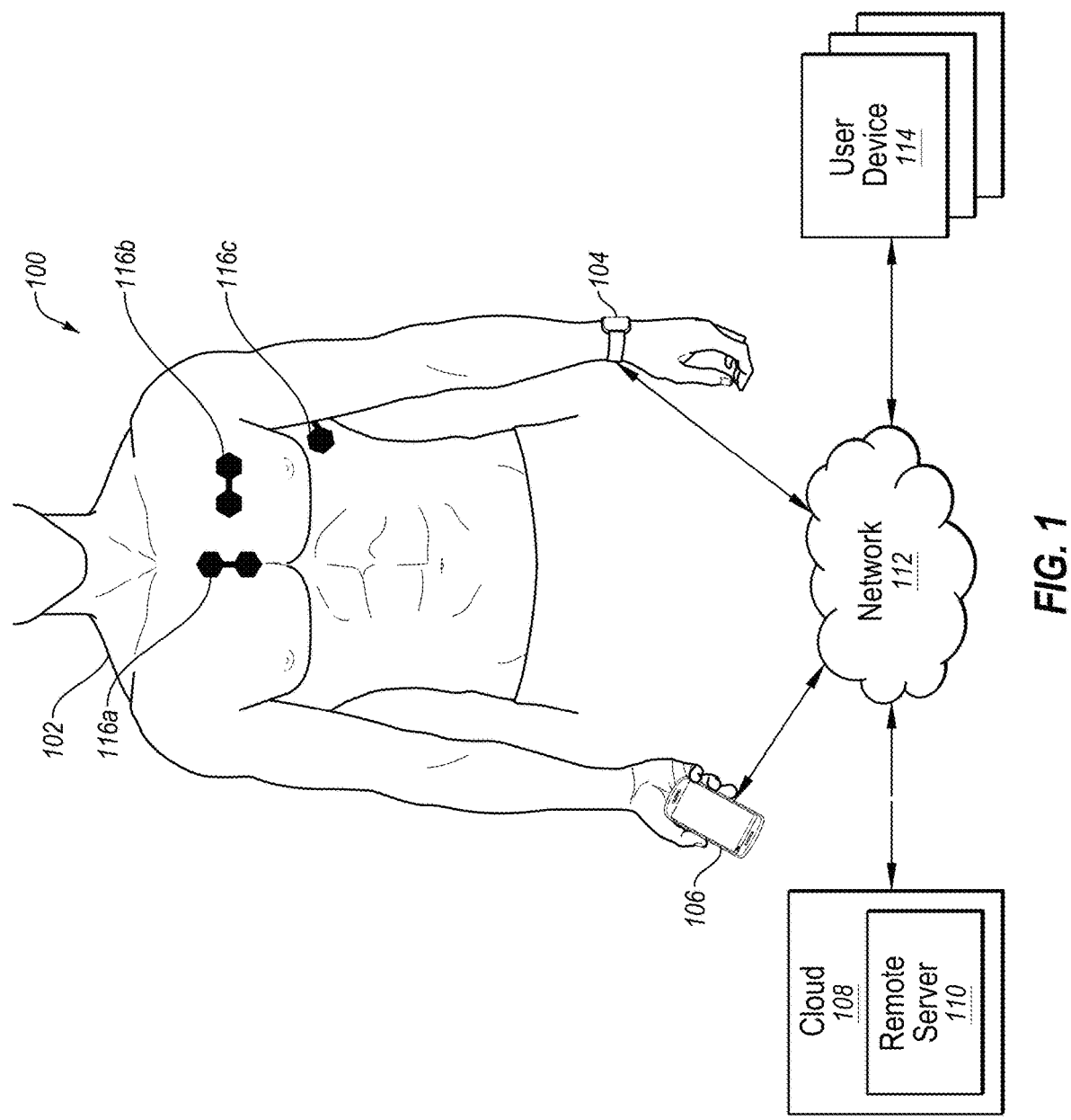
FIG. 1 illustrates an example environment in which some embodiments described herein can be implemented.

Some embodiments described herein generally relate to sensor fusion to validate and/or measure sound-producing behaviors of a subject. Such sound-producing behaviors can include sneezing, coughing, vomiting, shouting, or other sound-producing behaviors. The embodiments described herein may detect sound-producing behaviors in general and/or may categorize each of the sound-producing behaviors, e.g., as a sneeze, cough, vomiting, wheezing, shortness of breath, chewing, swallowing, masturbation, sex, a shout, or other particular type of sound-producing behavior.

An example implementation includes a wearable electronic device, such as a sticker with sensors, smart watch or other wrist-wearable electronic device, etc. that leverages sensor fusion to collect sensory data from disparate sources to validate or detect behaviors or biometric responses, such as sound-producing behaviors, with more certainty than would be possible when the sources are considered individually. In particular, the wearable electronic device may include multiple sensors that, at least in some circumstances, may be individually incapable of detecting sound-producing behaviors, at least with sufficient certainty. In aggregate, however, signals from the multiple sensors may be used to detect sound-producing behaviors, or to at least reduce the uncertainty associated with detection based on only one of the signals from only one of the sensors. While described as being implemented in a wearable electronic device, in other embodiments the various sensors may be distributed across multiple discrete devices that provide their sensor data to the wearable electronic device.

The various sensors include at least a microphone. The various sensors additionally include at least a second sensor configured to measure a parameter other than sound. For instance, the various sensors may additionally include at least one of an accelerometer, a gyro sensor, a Global Positioning System (GPS) sensor, an oxygen saturation sensor ($SO_2$) such as a pulse oximeter, a thermometer, a photoplethysmograph (PPG) sensor, an electrocardiograph (ECG) sensor, and/or an electrodermal activity (EDA) sensor. The wearable electronic device may include the microphone and as few as one, and up to all of the other sensors and/or other or different sensors.

The microphone may be used to record sound. The recorded sound may be processed to extract features indicative of discrete sound-producing behaviors, which extracted features may be used to detect sound-producing behaviors in general and/or specific types of sound-producing behaviors. While the term microphone is used, it will be appreciated that term includes any type of acoustic sensor that may be configured to detect sound waves and convert them into a readable signal such as an electronic signal. For example, a piezoelectric transducer, a condenser microphone, a moving-coil microphone, a fiber optic microphone, a MicroElectrical-Mechanical System (MEMS) microphone, etc. or any other transducer may be used to implement the microphone.

The accelerometer may be used to measure acceleration of at least a portion of the subject, such as the subject's wrist upon which the wearable electronic device that includes the accelerometer may be worn. The recorded acceleration may be processed to extract features that may be indicative (or not) of the sound-producing behaviors. For instance, when the subject sneezes, the subject's body (e.g., chest) upon which a sticker is placed may move violently and/or the wrist upon which the wearable electronic device is worn may move quickly to the subject's mouth as the subject attempts to cover the subject's mouth during the sneeze. The violent movement of the subject's body (e.g., chest) and/or of the wrist as the subject's mouth is covered may be identified in the acceleration recorded by the accelerometer. Alternatively or additionally, when the subject coughs, the subject's body (e.g., chest) and/or wrist may move less or not at all compared to when the subject sneezes, which data may be used to help distinguish between a cough and a sneeze in the sound recorded by the microphone. Alternatively or additionally, when the subject vomits, the subject may clutch their belly, a bowl, or make another movement that may be associated with and/or indicative of vomiting, which data may be extracted from the acceleration to confirm whether the subject has vomited. In some embodiments, the accelerometer may be used to measure the orientation of the body of the subject, such as whether they are walking, lying down, etc.

The gyro sensor may be used to measure angular velocity of at least a portion of the subject, such as the chest of subject upon which a sticker may be placed or the subject's wrist upon which the wearable electronic device that includes the gyro sensor may be worn. The angular velocity may be used in an analogous manner as the acceleration to confirm occurrence of sound-producing behaviors and/or to distinguish between different types of sound-producing behaviors based on measured movement (specifically angular velocity) of the subject's wrist or other body part to which the wearable electronic device is attached. E.g., specific movements (like moving a hand to cover a mouth while sneezing or coughing) associated with specific sound-producing behaviors may be identified in the measured angular velocity by extracting corresponding features therefrom. In some embodiments, the gyro sensor may be used to measure the orientation of the body of the subject, such as whether they are walking, lying down, etc.

The oxygen saturation sensor may be used to record blood oxygenation of the subject to generate a blood oxygenation level signal of the subject. Behaviors like shortness of breath or fits of coughing may correspond to a decrease in blood oxygen saturation levels. Other sound-producing behaviors may also correspond to variations in blood oxygen saturation levels. In these and other embodiments, data regarding the blood oxygen saturation levels may be used to extract features from the associated data, such as decreases in blood oxygen saturation, etc.

The thermometer may be used to record temperatures associated with the subject, including skin temperature and/or core body temperature. In some embodiments, the temperatures may correspond to conditions such as fever or elevated skin temperature for infection or other conditions that may accompany one or more sound-producing behaviors. For example, the thermometer may indicate that when experiencing high amounts of coughing, the subject was also experiencing a low-grade fever.

The PPG sensor may be used to record blood flow of the subject. Behaviors like sneezing may be sufficiently violent in at least some subjects that the jolt of a sneeze may manifest in the recorded blood flow. Alternatively or additionally, heart rate may be extracted from the recorded blood flow. In these and other embodiments, vomiting and/or nausea may often be associated with elevated heart rate such that an elevated heart rate determined from the recorded blood flow may confirm occurrence of vomiting.

The ECG sensor may be used to measure electrical activity of the subject's heart to determine the subject's heart rate and/or other parameters. Accordingly, ECG information recorded by the ECG sensor may be used in an analogous manner as the recorded blood flow.

The EDA sensor may be used to measure EDA of the subject's skin. The EDA information may manifest extractable features for at least some of the different types of sound-producing behaviors, such as at least vomiting.

Features may be extracted from the sound recorded by the microphone and from at least one other signal generated by at least one other sensor. When features from two or more of the sensors simultaneously indicate a sound-producing behavior, a sound-producing behavior may be detected with more certainty compared to detection based on a single one of the signals.

The embodiments described herein may be implemented using relatively cheap wearable electronic devices. Such wearable electronic devices may have a relatively constrained power supply (e.g., a relatively small battery) and/or a relatively constrained network connection (e.g., a Bluetooth connection on the order of tens of megabits per second (Mbit/s)). In such a wearable electronic device, it may be too power- and/or processor-intensive to process the data locally on the wearable electronic device using standard algorithms, and/or too bandwidth-intensive to upload the data to a remote server in the cloud for processing. Additionally, it may be overly power-intensive to continuously record audio data using the microphone.

Accordingly, embodiments described herein may be implemented in a manner in which the microphone may operate in a default "off" state in which it is not consuming power and not gathering data of audio around the subject. As events of interest are detected by the other less power-intensive sensors, a signal may be sent to the microphone so it may be turned on to capture audio data. For example, an accelerometer sensor may detect a rapid acceleration of the chest (such as experienced during a sneeze, vomiting, etc.) and in response to the detected acceleration, the microphone may be turned on for a three second window, after which the microphone may turn off again until another waking signal may be received.

Additionally, embodiments of the present disclosure may implement feature extraction to extract relevant features from data signals collected or received at the wearable electronic device. More resource-intensive processing may be limited to the relevant extracted features and/or underlying data. Alternatively or additionally, a quality score may be determined for each of the data signals. Data signals with a quality score that is too low (e.g., indicating a very noisy environment or low signal to noise ratio (SNR)) may be discarded altogether. Data signals with a quality score that is sufficiently high (e.g., indicating a relatively high SNR) may in some circumstances be used to the exclusion of other data signals. Data signals with quality scores between the two extremes may be used together to reduce uncertainty. Such quality scores may be calculated on a per segment or per window basis to, e.g., discard segments or windows that are too noisy and keep segments or windows that have sufficient SNR.

Feature extraction may be adaptive. For instance, feature extraction may be personalized, e.g., specifically adapted to each subject. As an example, feature extraction may learn to recognize and/or extract from data signals time-domain and/or frequency-domain features that are specific to each subject and/or may be more rigorous or extensive for subjects that belong to certain classes of subjects (e.g., subjects with known history of a particular condition). Alternatively or additionally, feature extraction may be adaptive to each environment in which subjects may be found. For instance, a relatively low resolution feature extraction may be implemented in low noise environments compared to a relatively higher resolution feature extraction in higher noise environments. Alternatively or additionally, feature extraction may be adaptive to a growing knowledge base or data set to update over time algorithms and/or state machines used to detect sound-producing behaviors.

In some embodiments, subjects may provide annotation inputs (or annotations). The annotations may be provided by the subjects of their own accord or in response to a request from the wearable electronic device. The annotations may be provided by input into the wearable electronic device or through other electronic devices. The annotations may confirm, or not, the occurrence of one or more sound-producing behaviors. For instance, if the data signals indicate the occurrence of a sound-producing behavior such as a sneeze, the wearable electronic device may output a message to ask the subject whether the subject just sneezed. The subject can respond with an appropriate input to confirm or deny the occurrence of the sneeze, which input may be received by the wearable electronic device as an annotation. The annotations may be fed back into the wearable electronic device and/or the cloud (e.g., a remote server), which may update algorithms and/or state machines used to detect sound-producing behaviors.

Wearable electronic devices as described herein can be used by numerous subjects. Annotations can be received from some or all of the subjects with significant network effects. For instance, as more subjects use the wearable electronic devices and more annotations are fed back, e.g., to the cloud to update the algorithms and/or state machines used to detect sound-producing behaviors, the algorithms and/or state machines may become increasingly accurate.

Reference will now be made to the drawings to describe various aspects of some example embodiments of the disclosure. The drawings are diagrammatic and schematic representations of such example embodiments, and are not limiting of the present disclosure, nor are they necessarily drawn to scale.

FIG. 1 illustrates an example environment 100 in which some embodiments described herein can be implemented. The environment 100 includes a subject 102 and a wearable electronic device 104. The environment 100 may additionally include a smartphone 106 (or other personal electronic device), a cloud computing environment (hereinafter "cloud 108") that includes at least one remote server 110, a network 112, multiple third party user devices 114 (hereinafter "user device 114" or "user devices 114"), and multiple third parties (not shown). The user devices 114 may include wearable electronic devices and/or smartphones of other subjects or users not illustrated in FIG. 1. The environment 100 may include one or more sensor devices 116, such as the devices 116a, 116b, and/or 116c.

The network 112 may include one or more wide area networks (WANs) and/or local area networks (LANs) that enable the wearable electronic device 104, the smartphone 106, the cloud 108, the remote server 110, the sensor devices 116, and/or the user devices 104 to communicate with each other. In some embodiments, the network 112 includes the Internet, including a global internetwork formed by logical and physical connections between multiple WANs and/or LANs. Alternately or additionally, the network 112 may include one or more cellular RF networks and/or one or more wired and/or wireless networks such as, but not limited to, 802.xx networks, Bluetooth access points, wireless access points, IP-based networks, or the like. The network 112 may also include servers that enable one type of network to interface with another type of network.

The environment 100 additionally includes one or more sensor devices 116. Each of the sensors of the sensor devices 116 are configured to generate data signals that measure parameters that may be indicative of behaviors and/or biometric responses of the subject 102. The measured parameters may include, for example, sound near the subject 102, acceleration of the subject 102 or of a chest, hand, wrist, or other part of the subject 102, angular velocity of the subject 102 or of a chest, hand, wrist, or other part of the subject 102, temperature of the skin of the subject 102, core body temperature of the subject 102, blood oxygenation of the subject 102, blood flow of the subject 102, electrical activity of the heart of the subject 102, EDA of the subject 102, or other parameters, one or more of which may be indicative of certain sound-producing behaviors of the subject 102, such as sneezing, coughing, vomiting, or shouting. The wearable electronic device 104, the smartphone 106, and/or the remote server 110 may be configured to determine or extract one or more features from the data signals and/or from data derived therefrom to detect sound-producing behaviors of the subject 102.

All of the sensors may be included in a single device, such as the sensor device 116, the wearable electronic device 104, and/or the smartphone 106. Alternately or additionally, the sensors may be distributed between two or more devices. For instance, one or each of the sensor devices 116, the wearable electronic device 104 or the smartphone 106 may include a sensor. Alternately or additionally, the one or more sensors may be provided as separate sensors that are separate from either of the wearable electronic device 104 or the smartphone 106. For example, the sensor devices 116 may be provided as separate sensors. In particular, the sensor devices 116 are separate from the wearable electronic device 104 and the smartphone 106, and is embodied in FIG. 1 as a chest-strap style heart rate monitor (e.g., electrocardiogram (ECG) sensor). In other embodiments, the distributed sensor devices 116 may include any of a discrete microphone, accelerometer, gyro sensor, thermometer, oxygen saturation sensor, PPG sensor, ECG sensor, EDA sensor, or other sensor. In some embodiments, each of the sensor devices 116 may include multiple sensors and multiple sensors devices may be used in analyzing the subject 102. For example, a first sensor device 116a may be positioned along a sternum of the subject 102; as another example, a second sensor device 116b may be positioned over the left breast to be over the heart; as an additional example, a third sensor device 116c may be positioned beneath the left arm of the subject 102. In these and other embodiments, the different sensor devices 116 at the different locations may be beneficial for a more robust set of data for analyzing the subject 102. For example, different locations of the sensor devices 116 may identify different features based on their respective locations proximate a chest cavity of the subject 102.

In some embodiments, the sensor devices 116 and/or the sensor(s) included in one or more of the wearable electronic device 104 and/or the smartphone 106 can include a discrete or integrated sensor attached to or otherwise born on the body of the subject 102. Various non-limiting examples of sensors that may be attached to the body of the subject 102 or otherwise implemented according to the embodiments described herein and that may be implemented as the sensor device 116 and/or as the sensor(s) included in the wearable electronic device 104 or the smartphone 106 include microphones, PPG sensors, accelerometers, gyro sensors, heart rate sensors (e.g., pulse oximeters), ECG sensors, EDA sensors, or other suitable sensors. In an example implementation, at least two sensors are provided in an integrated form (e.g., all sensors included in the wearable electronic device 104 or the smartphone 106) or in a distributed form (e.g., at least one sensor in the wearable electronic device 104 and at least one sensor in the smartphone 106 and/or as the sensor device 116). The two sensors may include a microphone and at least one of an accelerometer, a gyro sensor, a PPG sensor, an ECG sensor, or an EDA sensor.

As already mentioned, the sensors may each be configured to generate data signals, e.g., of sounds, acceleration, angular velocity, blood flow, electrical activity of the heart, EDA, or of other parameters of or near the subject 102. The data signals may be processed to determine a quality score for each and/or to extract features that may be indicative of sound-producing behaviors of the subject 102. The sound-producing behaviors may include, e.g., sneezing, coughing, vomiting, shouting, or other sound-producing behaviors.

The wearable electronic device 104 may be embodied as a portable electronic device and may be worn by the subject 102 throughout the day and/or at other times. The wearable electronic device 104 may be implemented as a sticker that is stuck to the chest of the subject 102, worn on a wrist of the subject 102 as illustrated in FIG. 1, may be carried in a pocket or clipped to a belt of the subject 102, or may be born in some other manner by the subject 102. As used herein, "born by" means carried by and/or attached to. The wearable electronic device 104 may be configured to, among other things, analyze signals collected by one or more sensors within the environment 100 to measure/detect sound-producing behaviors of the subject 102. In these and other embodiments, the wearable electronic device 104 may be a device dedicated for performing such functionality. The wearable electronic device 104 may include at least one onboard sensor for collecting such signals. Alternately or additionally, the smartphone 106 may include at least one sensor and may communicate signals collected by its onboard sensor to the wearable electronic device 104, and/or the wearable electronic device 104 may communicate with the sensor device 116 or other separate sensors to receive signals collected by the sensor device 116 or other separate sensor(s). The wearable electronic device 104 and/or the smartphone 106 may process the data signals collected from the sensors to detect one or more sound-producing behaviors of the subject 102. In these and other embodiments, the wearable electronic device 104 and/or the smartphone 106 may detect sound-producing behaviors by, e.g., executing one or more algorithms and/or state machines to classify extracted features as being indicative, or not, of sound-producing behaviors.

The wearable electronic device 104 and/or the smartphone 106 may be used by the subject 102 to perform journaling, including providing subjective annotations to confirm or deny the occurrence of sound-producing behaviors. Additional details regarding example implementations of journaling using a wearable electronic device or other device are disclosed in copending U.S. application Ser. No. 15/194,145, entitled WEARABLE DEVICE JOURNALING AND COACHING and filed on Jun. 27, 2016, which is incorporated herein by reference in its entirety. The subject 102 may provide annotations any time desired by the subject 102, such as after sneezing, coughing, vomiting, or shouting, and without being prompted by the wearable electronic device 104 or the smartphone 106. Alternatively or additionally, the subject 102 may provide annotations responsive to prompts from the wearable electronic device 104 or the smartphone 106. For instance, in response to detecting a sound-producing behavior based on data signals generated by one or more sensors, the wearable electronic device may provide an output to the subject 102 to confirm whether the detected sound-producing behavior actually occurred. The annotations may be provided to the cloud 108 and in particular to the remote server 110.

The remote server 110 may include a collection of computing resources available in the cloud 108. The remote server 110 may be configured to receive annotations and/or data derived from data signals collected by one or more sensors or other devices, such as the wearable electronic device 104 or smartphone 106, within the environment 100. Alternatively or additionally, the remote server 110 may be configured to receive from the sensors relatively small portions of the data signals. For instance, if the wearable electronic device 104 or smartphone 106 detects, with insufficient certainty, a sound-producing behavior of the subject 102, the wearable electronic device 104 or the smartphone 106 may upload to the remote server 110 a relatively small snippet of data for further analysis at the remote server 110. For instance, if the data signal includes an audio recording of the subject 102 and extracted features from the foregoing and/or other data signals indicate, but with insufficient certainty, that the subject 102 experienced a sound-producing behavior, a 5-10 second snippet of the data signal in which the sound-producing behavior appears to have occurred may be sent to the remote server 110. The remote server 110 may then apply more rigorous processing to the snippet to extract additional features and/or higher resolution features from the snippet than was applied at the constrained (e.g., power-constrained) wearable electronic device 104 and/or smartphone 106. Alternatively or additionally to the further processing, a live human may listen to the snippet uploaded to the remote sever 110 to determine whether the sound-producing behavior occurred.

In some embodiments, the wearable electronic device 104 and/or smartphone 106 may transmit the data signals to the remote server 110 such that the remote server may detect the sound-producing behavior. Additionally or alternatively, the wearable electronic device 104 and/or smartphone 106 may detect the sound-producing behavior from the data signals locally at the wearable electronic device 104 and/or smartphone 106. In these and other embodiments, a determination of whether or not to perform the detection of the sound-producing behavior locally or remotely may be based on capabilities of the processor of the local device, power capabilities of the local device, remaining power of the local device, communication channels available to transmit data to the remote server 110 (e.g., Wi-Fi, Bluetooth, etc.), payload size (e.g., how much data is being communicated), cost for transmitting data (e.g., a cellular connection vs. a Wi-Fi connection), etc. For example, if the wearable electronic device 104 includes a battery as a power source that is not rechargeable, the wearable electronic device 104 may include simple sound-producing behavior detection, and otherwise may send the data signals to the remote server 110 for processing. As another example, if the wearable electronic device 104 includes a rechargeable battery that is full, the wearable electronic device 104 may perform the detection locally when the battery is full or close to full and may decide to perform the detection remotely when the battery has less charge. As described in the present disclosure, the detection of the sound-producing behavior may include one or more steps, such as feature extraction, identification, and/or classification. In these and other embodiments, any of these steps or processes may be performed at any combination of devices such as at the wearable electronic device 104, the smartphone 106, and/or the remote server 110. For example, the wearable electronic device 104 may collect data and perform some processing on the data (e.g., collecting audio data and performing a power spectral density process on the data), provide the processed data to the smartphone 106, and the smartphone 106 may extract one or more features in the processed data, and may communicate the extracted features to the remote server 110 to classify the features into one or more sound producing behaviors.

In some embodiments, an intermediate device may act as a hub to collect data from the wearable electronic device 104 and/or the smartphone 106. For example, the hub may collect data over a local communication scheme (Wi-Fi, Bluetooth, near-field communications (NFC), etc.) and may transmit the data to the remote server 110. In some embodiments, the hub may act to collect the data and periodically provide the data to the remote server 110, such as once per week.

The remote server 110 may maintain one or more of the algorithms and/or state machines used in the detection of sound-producing behaviors by the wearable electronic device 104 and/or the smartphone 106. In some embodiments, annotations or other information collected by, e.g., the wearable electronic device 104, the smartphone 106, and/or the user devices 114, for multiple subjects may be fed back to the cloud 108 to update the algorithms and/or state machines. This may advantageously lead to significant network effects, e.g., as more information is collected from more subjects, the algorithms and/or state machines used to detect sound-producing behaviors may be updated to become increasingly accurate and/or efficient. The updated algorithms and/or state machines may be downloaded from the remote server 110 to the wearable electronic device 104, the smartphone 106, and/or the user devices 114 to, e.g., improve detection.

Figure 2:
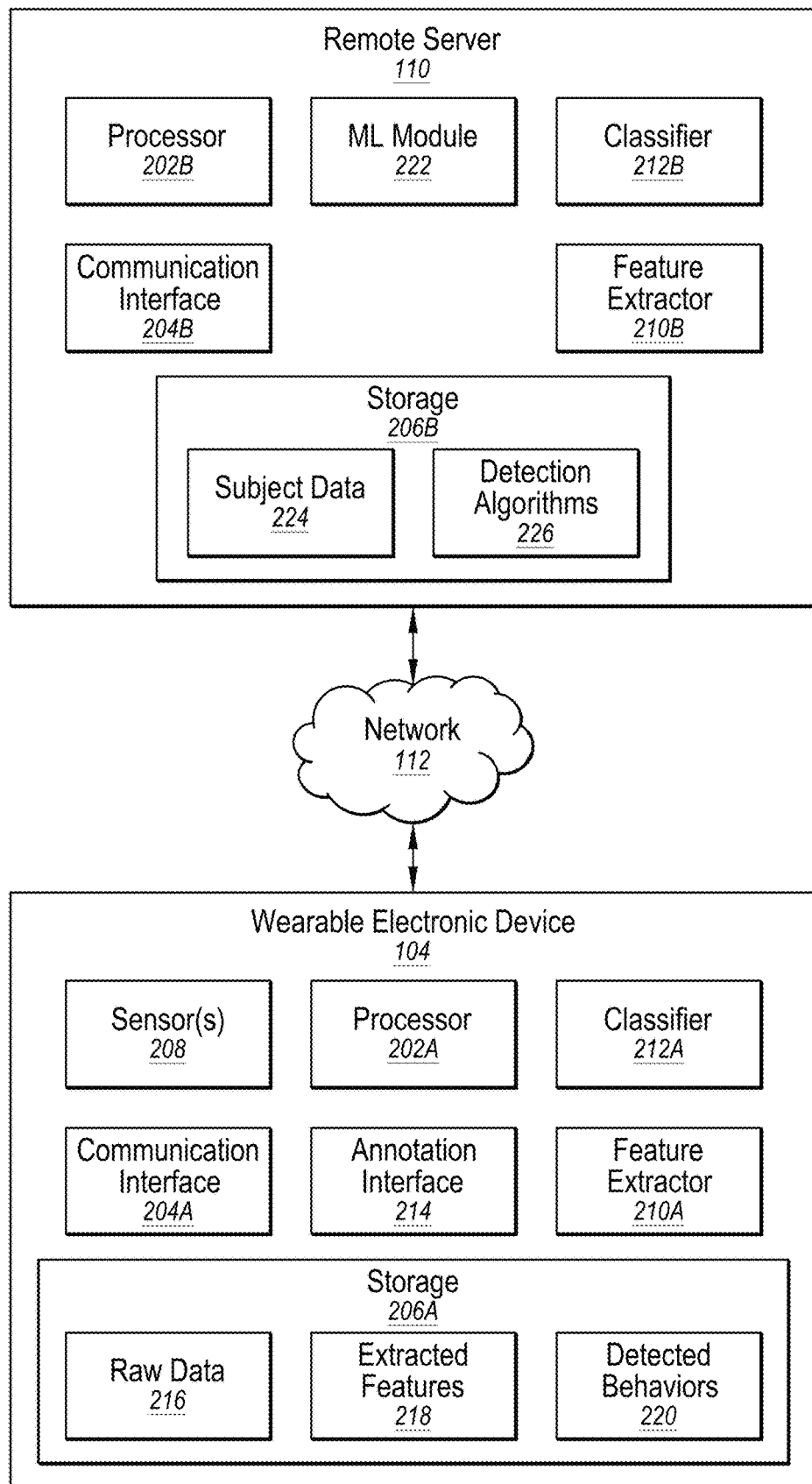
FIG. 2 is a block diagram of a wearable electronic device and a remote server of FIG. 1.

FIG. 2 is a block diagram of the wearable electronic device 104 and remote server 110 of FIG. 1, arranged in accordance with at least one embodiment described herein. Each of the wearable electronic device 104 and the remote server 110 may include a processor 202A or 202B (generically "processor 202" or "processors 202"), a communication interface 204A or 204B (generically "communication interface 204" or "communication interfaces 204"), and a storage and/or memory 206A or 206B (generically "storage 206"). Although not illustrated in FIG. 2, the smartphone 106 (or other personal electronic device) of FIG. 1 may be configured in a similar manner as the wearable electronic device 104 as illustrated in FIG. 2. For instance, the smartphone 106 may include the same, similar, and/or analogous elements or components as illustrated in FIG. 2.

Each of the processors 202 may include an arithmetic logic unit, a microprocessor, a general-purpose controller, or some other processor or array of processors, to perform or control performance of operations as described herein. The processors 202 may be configured to process data signals and may include various computing architectures including a complex instruction set computer (CISC) architecture, a reduced instruction set computer (RISC) architecture, or an architecture implementing a combination of instruction sets. Although each of the wearable electronic device 104 and the remote server 110 of FIG. 2 includes a single processor 202, multiple processor devices may be included and other processors and physical configurations may be possible. The processor 202 may be configured to process any suitable number format including, but not limited to two's compliment numbers, integers, fixed binary point numbers, and/or floating point numbers, etc. all of which may be signed or unsigned.

Each of the communication interfaces 204 may be configured to transmit and receive data to and from other devices and/or servers through a network bus, such as an I$^2$C serial computer bus, a universal asynchronous receiver/transmitter (UART) based bus, or any other suitable bus. In some implementations, each of the communication interfaces 204 may include a wireless transceiver for exchanging data with other devices or other communication channels using one or more wireless communication methods, including IEEE 802.11, IEEE 802.16, BLUETOOTH®, Wi-Fi, Zigbee, near field communication (NFC), or another suitable wireless communication method.

The storage 206 may include a non-transitory storage medium that stores instructions or data that may be executed or operated on by a corresponding one of the processors 202. The instructions or data may include programming code that may be executed by a corresponding one of the processors 202 to perform or control performance of the operations described herein. The storage 206 may include a non-volatile memory or similar permanent storage media including a flash memory device, an electrically erasable and programmable read only memory (EEPROM), a magnetic memory device, an optical memory device, or some other mass storage for storing information on a more permanent basis. In some embodiments, the storage 206 may also include volatile memory, such as a dynamic random access memory (DRAM) device, a static random access memory (SRAM) device, or the like.

The wearable electronic device 104 may additionally include one or more sensors 208, a feature extractor 210A, a classifier 212A, and/or an annotation interface 214. The storage 206A of the wearable electronic device 104 may include one or more of data 216, extracted features 218, and/or detected sound-producing behaviors 220 (hereinafter "detected behaviors 220").

The sensor 208 may include one or more of a microphone, an accelerometer, a gyro sensor, a PPG sensor, an ECG sensor, or an EDA sensor. In embodiments in which the wearable electronic device 104 includes or uses a single sensor 208 to detect sound-producing behaviors of the subject 102, one or more other sensors such as the discrete sensor 114 and/or an integrated sensor of the smartphone 106 may communicate one or more corresponding data signals to the wearable electronic device 104 (e.g., through the communication interface 204A). In these and other embodiments, data signals from two or more sensors may be processed at a constrained device such as the wearable electronic device 104 to detect sound-producing behaviors with greater certainty than could be done with a single data signal itself. While only a single sensor 208 is illustrated in FIG. 2, more generally the wearable electronic device 104 may include one or more sensors.

In some embodiments, the wearable electronic device 104 may include multiple sensors 208, with a trigger from one sensor 208 causing another sensor 208 to receive power and start capturing data. For example, an accelerometer, gyro sensor, EKG, etc. may trigger a microphone to begin receiving power to capture audio data.

The feature extractor 210A, the classifier 212A, and the annotation interface 214 may each include code such as computer-readable instructions that may be executable by the processor 202A of the wearable electronic device 104 to perform or control performance of one or more methods or operations as described herein. For instance, the feature extractor 210A may in some embodiments divide data signals into frames and/or windows and extract one or more features from the data signals in the time domain and/or the frequency domain. The classifier 212A may in some embodiments classify frames and/or windows as indicative of sound-producing behaviors based on the extracted features from the feature extractor 210A and/or may perform additional and/or more robust feature extraction on some of the extracted features and/or underlying data. In some embodiments, the classifier 212A may identify one or more wake-up events in underlying data that excludes audio data.

Based on the identification of such a feature associated with a wake-up event, the processor 202A may send a signal to cause the microphone to receive power and begin capturing audio data. The annotation interface 214 may in some embodiments prompt the subject 102 for and/or receive from the subject 102 annotations. An example method that may be performed or controlled by execution of one or more of the feature extractor 210A, the classifier 212A, and/or the annotation interface 214 is described below with respect to FIG. 4. The feature extractor 210A, the classifier 212A, and the annotation interface 214 may be stored in the storage 206A or other non-transitory medium.

The data 216 may include some or all of each data signal generated by each sensor 208. In an example embodiment, portions of each data signal may be stored temporarily in the storage 206A for processing (e.g., feature extraction) and may be discarded after processing, to be replaced by another newly collected portion of the data signal. Alternatively or additionally, one or more portions of one or more data signals may be retained in storage 206A even after being processed. In some embodiments, certain sensors may continuously gather data, while others may intermittently capture data. For example the data 216 may contain continuous data from an accelerometer but only a few windows of data from a microphone.

In some embodiments, the size of the data 216 stored may be based on the capacity of the storage 206A. For example, if the storage 206A includes large amounts of storage, longer windows of time of the data 216 may be stored, while if the storage 206A includes limited amounts of storage, shorter windows of time of the data 216 may be stored. As another example, if the storage 206A includes large amounts of storage, multiple short windows of time of the data 216 may be stored, while if the storage 206A includes limited amounts of storage, a single windows of time of the data 216 may be stored.

The extracted features 218 may include features extracted by the feature extractor 210A and/or the classifier 212A that may be indicative of sound-producing behaviors of interest, sound-producing behaviors or other sounds not of interest, and/or undetermined. Examples of sound-producing behaviors or other sounds not of interest may include the subject 102 talking, clearing his/her throat, sniffling, or sounds produced by other people or objects near or around the subject 102. In an example embodiment, extracted features for sound-producing behaviors or other sounds that are not of interest may be discarded and features indicative of sound-producing behaviors of interest and/or undetermined may be retained. Alternatively or additionally, extracted features indicative of sound-producing behaviors of interest and/or undetermined may be discarded after being further processed and/or classified, e.g., by the classifier 212A, and/or after being reported to the remote server 110.

The detected behaviors 220 may include sound-producing behaviors of interest and/or other sound-producing behaviors detected based on one or more of the extracted features 218. Each of the detected behaviors 220 may include a classification of the detected behaviors, a time at which the detected behaviors occurred, and/or other information.

In some embodiments, the sensors 208 may include a microphone and at least one other sensor. The processor 202A may continually monitor the data 216 from the other sensor other than the microphone (e.g., an accelerometer). The data 216 from the other sensor may be continuously gathered and discarded along a running window (e.g., storing a window of 10 seconds, discarding the oldest time sample as a new one is obtained). In these and other embodiments, as the feature extractor 210A identifies a feature for waking up the microphone (e.g., a rapid acceleration potentially identified as a sneeze), the data 216 may include a window of audio data. The feature extractor 210A may analyze both the data 216 from the other sensor and the data 216 from the microphone to extract one or more features 218.

Referring to the remote server 110, it may additionally include a feature extractor 210B, a classifier 212B, and/or a machine learning (ML) module 222. The storage 206B of the remote server 110 may include one or more of subject data 224 and/or detection algorithms 226. The subject data 224 may include snippets of data, extracted features, detected behaviors, and/or annotations received from wearable electronic devices and/or smartphones used by subjects, such as the wearable electronic device 104. The detection algorithms 226 may include algorithms and/or state machines used by the wearable electronic device 104 and/or the remote server 110 in the detection of, e.g., sound-producing behaviors.

The feature extractor 210B, the classifier 212B, and the ML module 222 may each include code such as computer-readable instructions that may be executable by the processor 202B of the remote server 110 to perform or control performance of one or more methods or operations as described herein. For instance, one or both of the feature extractor 210B or the classifier 212B may perform the same or analogous operations as one or both of the classifier 212A or feature extractor 210A of the wearable electronic device 104. For instance, the feature extractor 210B and the classifier 212B may in some embodiments perform the same and/or more robust, more processor-intensive, more power-intensive and/or higher resolution processing of snippets of data signals, extracted features, and/or other data received from the wearable electronic device 104 as compared to the feature extractor 210A and the classifier 212A. The ML module 222 may evaluate some or all of the subject data 224 to generate and/or update the detection algorithms 226. For instance, annotations together with extracted features and/or detected behaviors or other subject data 224 may be used as training data by the ML module 222 to generate and/or update the detection algorithms 226. Updated detection algorithms 226 used in feature extraction, classification, or other aspects of sound-producing behavior detection may then update one or more of the feature extractors 210A, 210B and/or classifiers 212A, 212B or other modules in one or both of the remote server 110 and wearable electronic device 104.

Figure 3A:
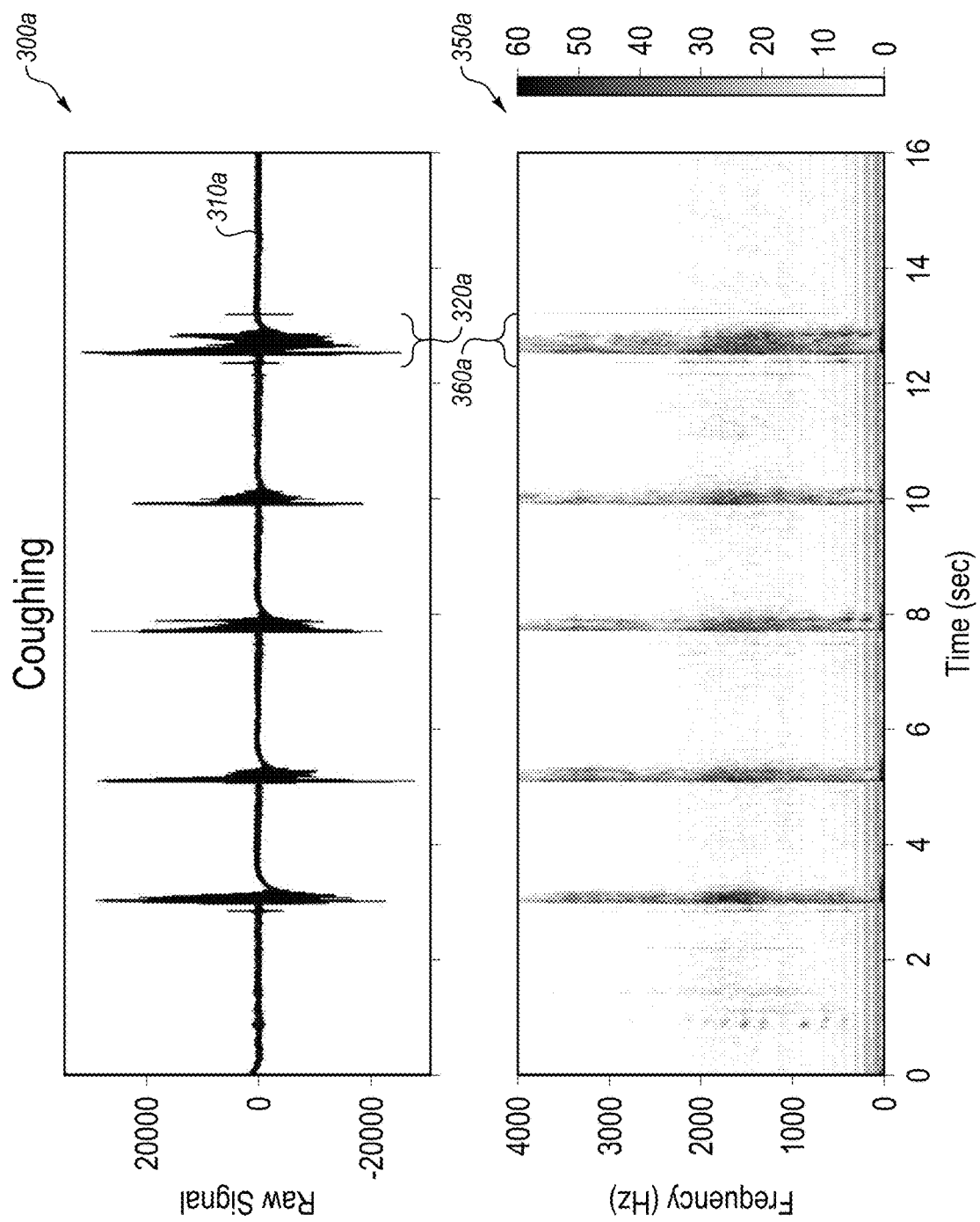
FIGS. 3A-3I include various examples of audio data signal and various extracted features.
Figure 3B:
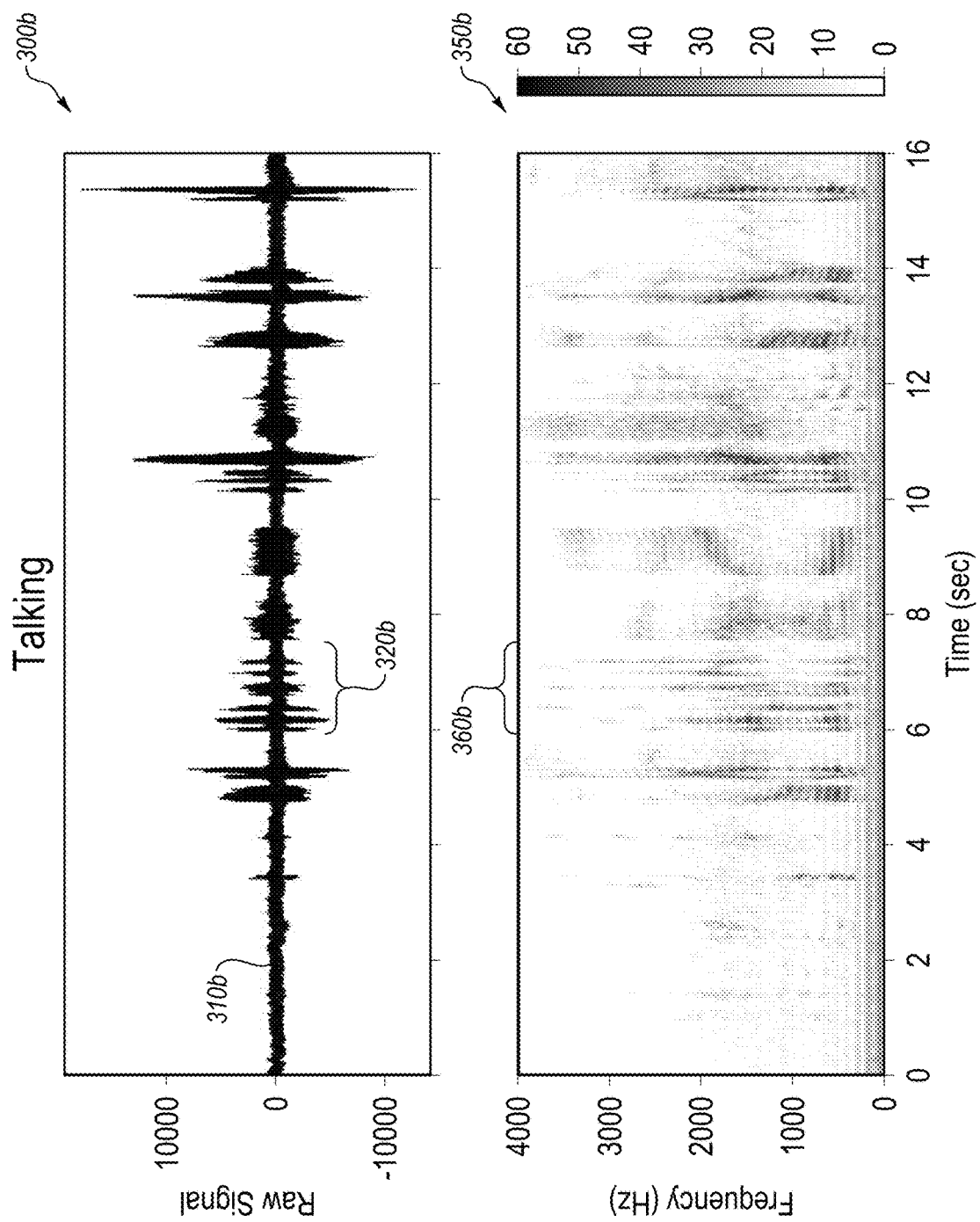
Figure 3C:
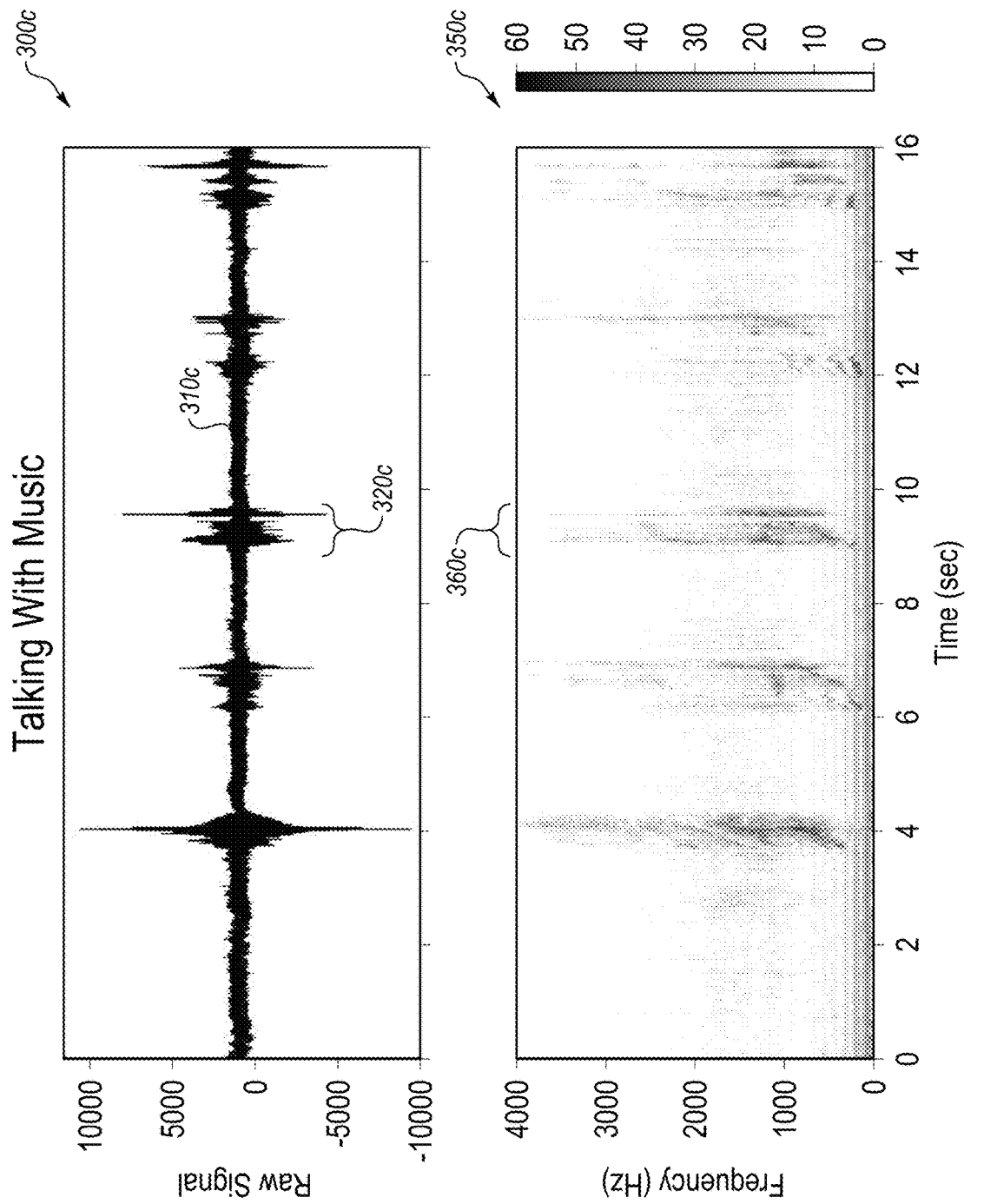
Figure 3D:
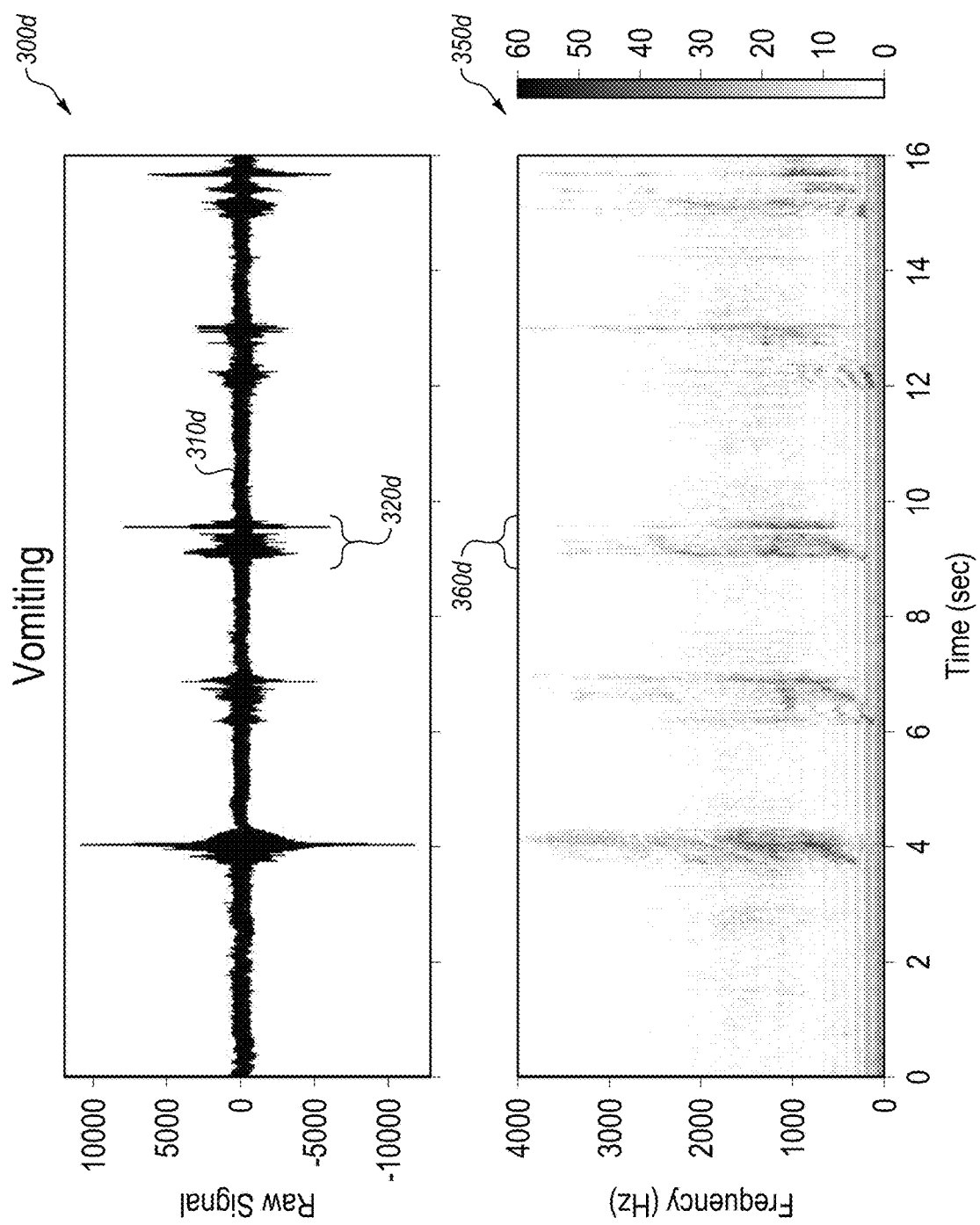
Figure 3E:
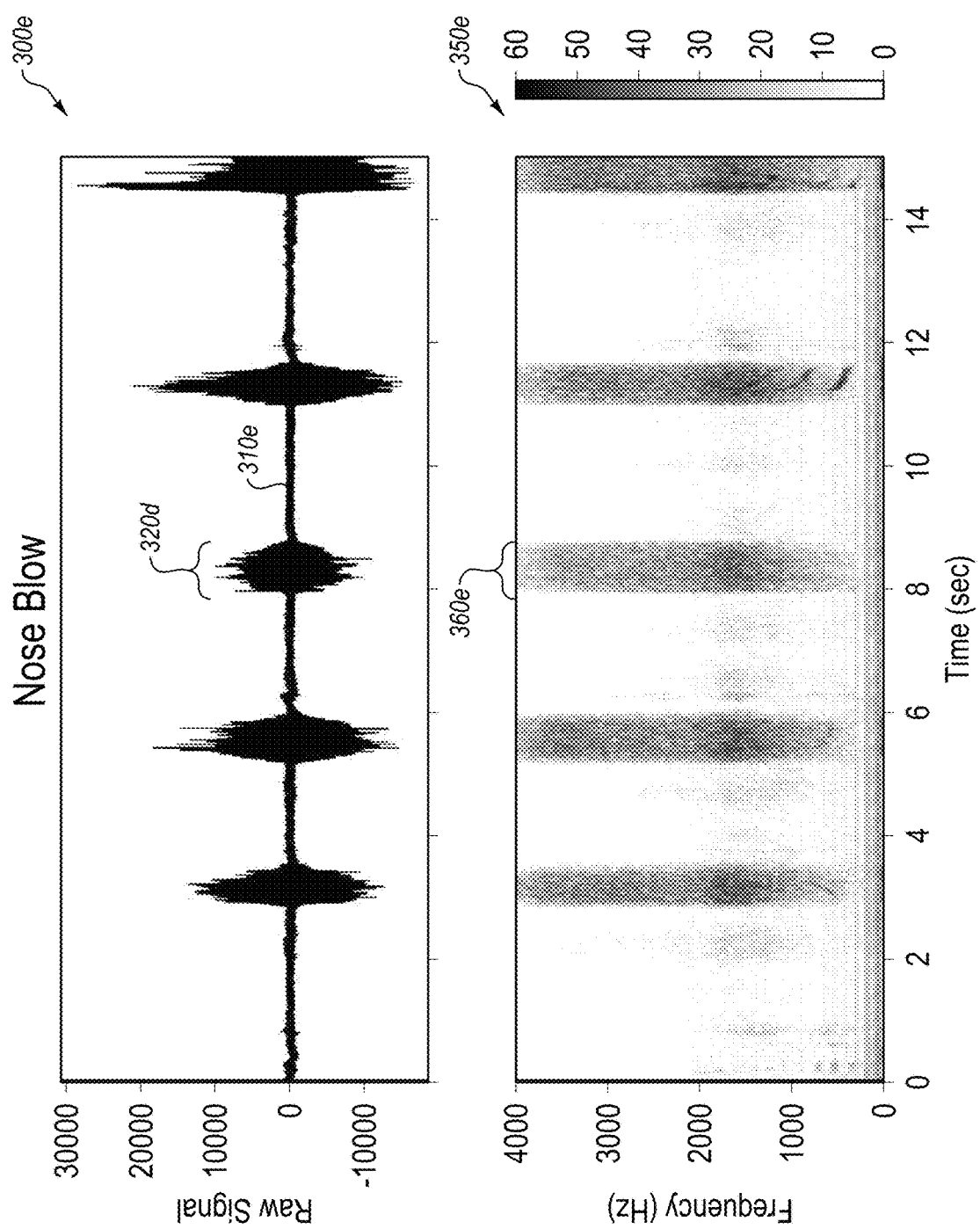
Figure 3F:
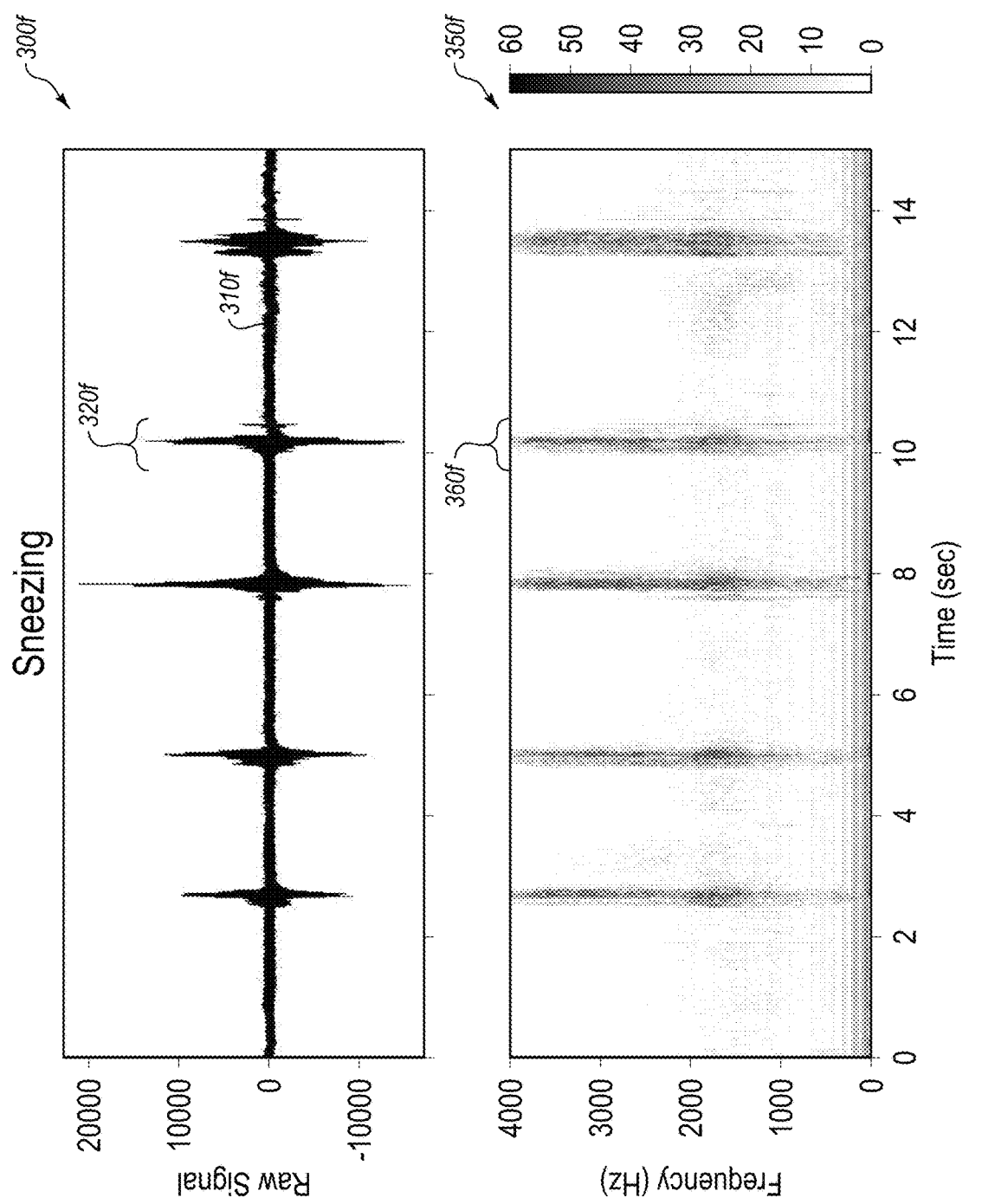
Figure 3G:
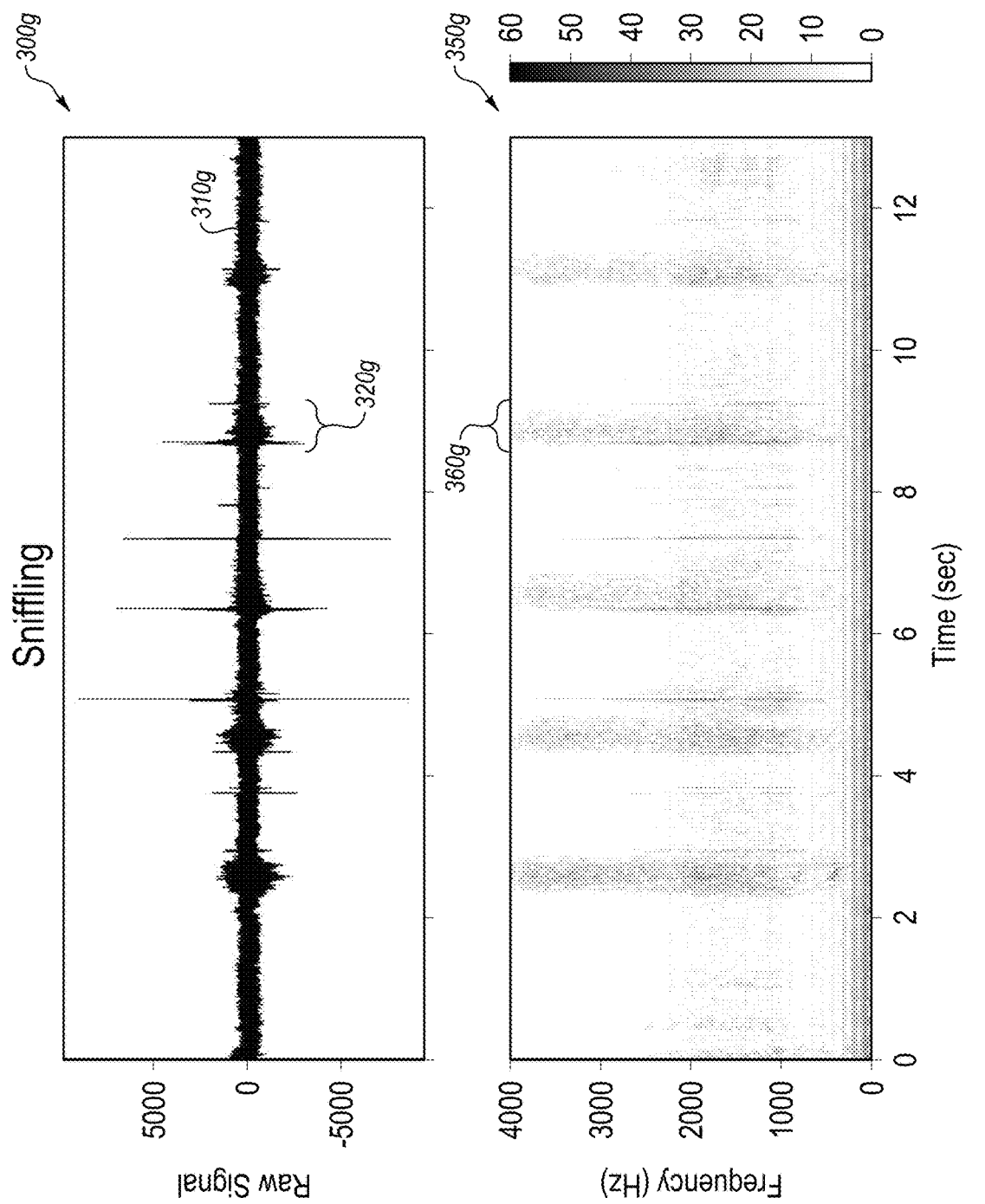
Figure 3H:
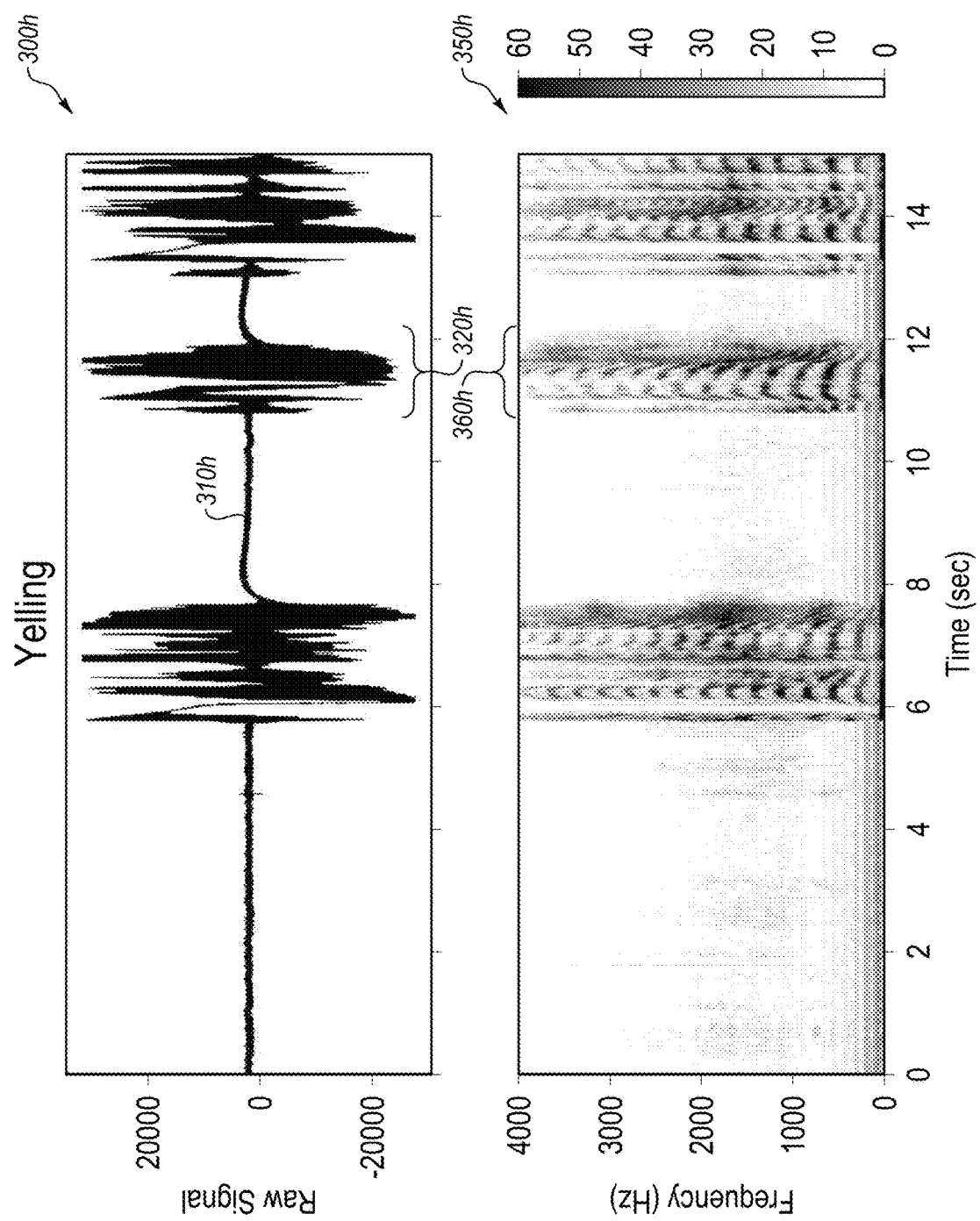
Figure 3I:
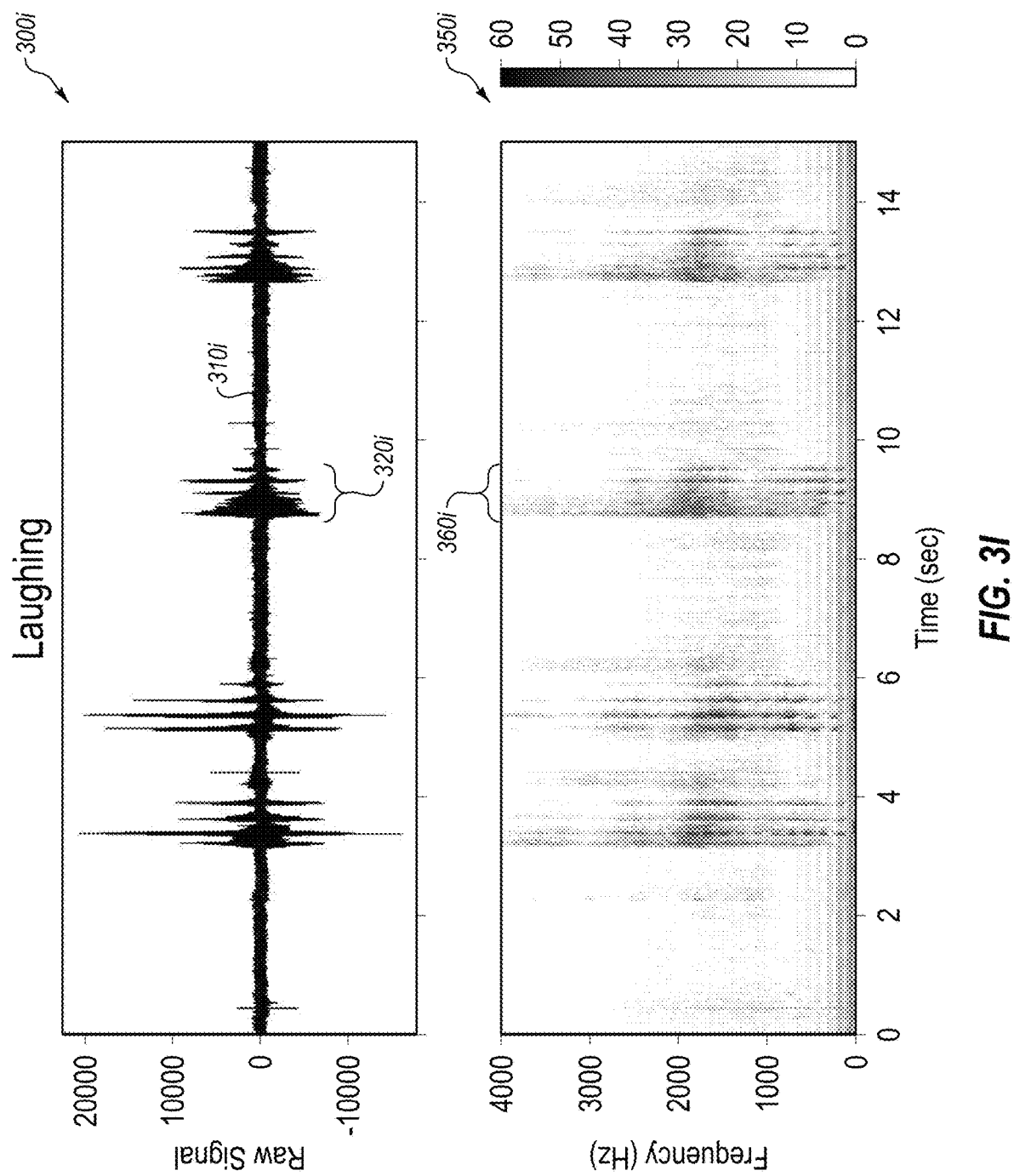

FIGS. 3A-3I include various examples of audio data signal and various extracted features, arranged in accordance with at least one embodiment described herein. Each of FIGS. 3A-3I illustrate a series of different sound-producing behaviors in either or both of an audio data plot (300), and a power spectral density (PSD) spectrogram computed using short-time Fourier transform or otherwise processed audio data plot (350). FIG. 3A illustrates coughing, FIG. 3B illustrates talking, FIG. 3C illustrates talking with music, FIG. 3D illustrates vomiting, FIG. 3E illustrates nose blowing, FIG. 3F illustrates sneezing, FIG. 3G illustrates sniffling, FIG. 3H illustrates yelling, and FIG. 3I illustrates laughing.

As illustrated in FIG. 3A, the audio data plot 300a may include an amplitude signal 310a representing the audio data as captured by a microphone or other comparable sensor. The amplitude signal 310a may include one or more features 320a. For example, there may be a feature at approximately 3 seconds, 5 seconds, 8 seconds, 10 seconds, and 13 seconds.

In addition to the audio data plot 300a, FIG. 3A may include a processed audio data plot 350a. The processed audio data plot 350a may include one or more features 360a that may correspond to the one or more features 320a. For example, the feature 360a at approximately 13 seconds may correspond to the feature 320a of the amplitude signal 310a at approximately 13 seconds.

In some embodiments, the processed audio data plot 350a may represent a time-frequency analysis of the amplitude signal 310a. In some embodiments, such a time-frequency analysis may be one in which the original audio data may not be recreated from the output of the time-frequency analysis. For example, the processed audio data plot 350a may include a power spectral density (PSD) spectrogram plot. In these and other embodiments, the processed audio data plot 350a may represent a depiction of the density of power at different frequencies at different times.

In some embodiments, the use of such an approach may facilitate a more secure and/or more private implementation. For example, the processed audio data plot 350a may be one in which the original audio data (e.g., the amplitude signal 310a) may not be recreated from the processed audio data plot 350a. In these and other embodiments, if there is talking in the original audio data, such a process may provide confidence that a third party and/or the party providing the device to capture the audio data will not be listening to conversations of the user.

In some embodiments, features such as the feature 360a may be identified based on pattern matching of the feature 360a with known patterns of any of the sound-producing behaviors (e.g., coughs, sneezes, etc.). Additionally or alternatively, such pattern matching may produce ambiguous results, or more than one potential sound-producing behavior as causing the feature, and accelerometer data or any other sensor data may be included in the feature identification process to facilitate an improved confidence in identification of the feature.

In some embodiments, rather than extracting features from data such as combinations of audio data and accelerometer data, features may be extracted from representations of the data using a time-frequency analysis. For example, the audio data may be converted from the time domain to the frequency domain over a sliding time window using a short-time Fourier transform based on Fast Fourier Transform (FFT). The resulting PSD spectrogram of the audio data may be analyzed to extract features that correlate with behaviors such as sneezing, coughing, vomiting, shouting, etc. In some embodiments, the window of audio data in the PSD spectrogram may be compared with data from one or more other sensors to increase the confidence in the identification of the feature. For example, analysis of the audio data in the PSD spectrogram may provide a 65% probability that an event is a cough, and a 25% probability it is a sneeze, and a 10% chance it is neither, while if data of an accelerometer is included in the analysis, the probabilities may change to an 80% probability that the event is a cough, and a 12% probability that it is a sneeze, and an 8% probability that it is neither.

In some embodiments, feature detection may be performed in any other manner, such as that generally described by, e.g., Xiao Sun et al., SymDetector: Detecting Sound-Related Respiratory Symptoms Using Smartphones, available at http://www.cse.psu.edu/~wwh5068/paper/ubicomp-xiaosun15.pdf (accessed on Nov. 10, 2016, hereinafter "Sun"). For instance, the amplitude signal 310a may be segmented into non-overlapped frames of 50 milliseconds (ms) for feature extraction, where several continuous frames may be grouped together as a window to be processed as a unit. Extracted features may include one or more of root mean square (RMS), above α-mean ratio (AMR), average of top k RMSs (ATR), and/or other features as disclosed by Sun. The various features may be generally used to (1) identify potential sound-producing behaviors which may include sound-producing behaviors of interest, those not of interest, and other discrete sounds not of interest, (2) filter out all sounds not of interest, and (3) distinguish the sound-producing behaviors from each other. For instance, the RMS may be a measure of energy contained in each acoustic frame and can be used to identify (and discard) those frames that do not have any potential sounds of interest. The AMR may be a measure of those windows that include discrete acoustic events, where a low AMR indicates a discrete acoustic event. The other features that may be extracted as disclosed by Sun may be used to distinguish sounds that are not of interest according to embodiments disclosed herein (such as talking, throat clearing, sniffling, door closing) from sounds that are of interest according to embodiments disclosed herein (e.g., coughing, sneezing, and/or others).

In some embodiments, certain considerations may be involved in implementing the present disclosure based on a location of the sensor and/or a gender of the subject. For example, if the sensors are physically attached to the chest of the subject (e.g., via a sticker), the microphone may be oriented to be listening to the chest cavity of the subject, rather than oriented to be listening to the ambient surroundings of the subject, in a similar manner to how a physician might orient a stethoscope. In these and other embodiments, the audio data may be more attuned to certain frequencies and/or patterns depending on the event of interest. For example, a cough may cause a certain spike in a certain frequency when heard via an ambient-listening microphone, but may include two or more related spike in frequencies when heard via a microphone oriented inwardly towards the chest cavity of the subject.

In some embodiments, the gender of the subject may modify or otherwise adjust the patterns and/or frequencies observed when identifying various events. For example, for men, pectoral muscles may impede or alter the frequencies observed for various events. As another example, breast tissue for females may impede or alter the frequencies observed for various events. In light of such variations, events may be identified, the microphone may be triggered to wake up to begin capturing audio, etc. based on a gender of the subject.

In some embodiments, the orientation of the microphone may yield increased insight into various aspects of the event. For example, if an event is identified as a cough, by having the microphone oriented against the chest of the subject, the audio data collected by the microphone may be able to detect whether there are any particular aspects of the event of note, such as any rattles or whistles associated with the cough, whether or not there is any buildup of mucus, phlegm, or other constriction of airways heard in the cough, etc.

According to embodiments described herein, data signals collected in practice may be relatively noisy. Thus, multiple data signals (e.g., audio, acceleration, angular velocity, blood flow, ECG, and/or EDA data signals) may be collected to extract features from each that may reduce uncertainty in the detection of sound-producing behaviors. For instance, if a first data signal is somewhat noisy at a particular time such that a feature or features extracted from the first data signal suggest the occurrence of a sound-producing behavior but are somewhat ambiguous or unclear, a feature or features extracted from a second data signal for the same particular time that also suggest or even more clearly indicate the occurrence of the sound-producing behavior may reduce the uncertainty by considering features from both data signals. Alternatively or additionally, uncertainty may be reduced by considering features from three or more data signals.

In still other implementations, different sound-producing behaviors may have similar characteristics or features in a given data signal even if the given data signal is relatively clean, but may have more distinct characteristics or features in a different data signal that can be used to discriminate between the two. For instance, sneezing and coughing may be somewhat similar in duration and amplitude in an audio data signal even if the audio data signal is relatively clean. To discriminate between the two to detect whether a sound-producing behavior is a sneeze or a cough, a different data signal may be used that may have less ambiguity in characteristics and/or features between sneezing and coughing.

Accordingly, uncertainty in detecting sound-producing behaviors can be reduced by using data signals from two or more different sensors that generate data signals relating to different parameters. By using at least two different sensors that detect different parameters, noise or ambiguity that may be present in one of the data signals may be absent from the other.

Embodiments described herein may extract features from data signals, where the features may be indicative of a sound-producing behavior. For instance, as illustrated by the amplitude signal 310a in FIG. 3A, sound-producing behaviors may be characterized by a spike in amplitude in the amplitude signal 310a, a spike in the processed audio data plot 350a, and/or by other characteristics and/or features. Alternatively or additionally, the particular sound-producing behaviors of interest may be characterized by certain movements or physiological responses that may be measurable by other sensors as described herein. Features indicative of such characteristics may be extracted from a corresponding data signal. Examples of such features may include one or more of rapid acceleration of the chest during a cough, a lower and more prolonged acceleration during vomiting, etc.

In an example implementation, feature extraction and classification may occur substantially as follows. Audio data or other data may be identified as including a feature. For example, as illustrated in FIG. 3A, the spike in amplitude around 13 seconds may indicate that a feature may have occurred at that time. The associated audio data (or all the audio data) may be processed for time-frequency analysis (e.g., a power spectral density (PSD) spectrogram). Additionally or alternatively, the processing may include filtering or other analysis. In some embodiments, features may be extracted by processing all audio data within a time window after a wake-up event experienced by an accelerometer. After extracting one or more features, a pattern matching process may be performed on the extracted features. For example, the PSD spectrogram of the extracted feature may be compared to multiple reference PSD spectrograms of known sound-producing behaviors. In some embodiments, these reference PSD spectrograms may be applicable to any number of users. Additionally or alternatively, the reference PSD spectrograms may be generated during an enrollment session for a given user (e.g., when receiving a wearable device with sensors, the user may be asked to cough, blow their nose, read a passage, etc. and the associated sensor responses for such sound-producing behaviors may be collected and stored, including generation of PSD spectrograms on the audio and/or other data associated with the reference sound-producing behaviors). In addition or alternatively to a pattern matching process, any other categorization process, such as a machine learning process (e.g., logistic regression, decision trees, neural networks, etc.) may be used to identify to which category of sound-producing behavior the PSD spectrogram belongs.

As illustrated in FIG. 3B, the audio data plot 300b may include the amplitude signal 310b of a user talking. The amplitude signal 310b may include one or more features 320b. For example, there may be intermittent features between approximately 5 seconds and 14 seconds, and approximately 15 seconds.

In addition to the audio data plot 300b, FIG. 3B may include a processed audio data plot 350b. The processed audio data plot 350b may include one or more features 360b that may correspond to the one or more features 320b. For example, the feature 360b at approximately 5-7 seconds may correspond to the feature 320b of the amplitude signal 310b at approximately 5-7 seconds.

As illustrated in FIG. 3C, the audio data plot 300c may include the amplitude signal 310b of a user talking with music. The amplitude signal 310c may include one or more features 320c. For example, there may be intermittent features between approximately 6 seconds and 8 seconds, and approximately 9 seconds and 15 seconds.

In addition to the audio data plot 300c, FIG. 3C may include a processed audio data plot 350c. The processed audio data plot 350c may include one or more features 360c that may correspond to the one or more features 320c. For example, the feature 360c at approximately 9-10 seconds may correspond to the feature 320c of the amplitude signal 310c at approximately 9-10 seconds.

As illustrated in FIG. 3D the audio data plot 300d may include the amplitude signal 310d of a user vomiting. The amplitude signal 310d may include one or more features 320d. For example, there may be intermittent features at approximately 4 seconds, 6 seconds, 9 seconds, 12 seconds, and 15 seconds.

In addition to the audio data plot 300d, FIG. 3D may include a processed audio data plot 350d. The processed audio data plot 350d may include one or more features 360d that may correspond to the one or more features 320d. For example, the feature 360d at approximately 9 seconds may correspond to the feature 320d of the amplitude signal 310d at approximately 9 seconds.

As illustrated in FIG. 3E the audio data plot 300e may include the amplitude signal 310e of a user blowing his nose. The amplitude signal 310e may include one or more features 320e. For example, there may be intermittent features at approximately 3 seconds, 5 seconds, 8 seconds, 11 seconds, and 15 seconds.

In addition to the audio data plot 300e, FIG. 3E may include a processed audio data plot 350e. The processed audio data plot 350e may include one or more features 360e that may correspond to the one or more features 320e. For example, the feature 360e at approximately 8 seconds may correspond to the feature 320e of the amplitude signal 310e at approximately 8 seconds.

As illustrated in FIG. 3F the audio data plot 300f may include the amplitude signal 310f of a user sneezing. The amplitude signal 310f may include one or more features 320f. For example, there may be intermittent features at approximately 3 seconds, 5 seconds, 8 seconds, 10 seconds, and 13 seconds.

In addition to the audio data plot 300f, FIG. 3F may include a processed audio data plot 350f. The processed audio data plot 350f may include one or more features 360f that may correspond to the one or more features 320f. For example, the feature 360f at approximately 10 seconds may correspond to the feature 320f of the amplitude signal 310f at approximately 10 seconds.

As illustrated in FIG. 3G the audio data plot 300g may include the amplitude signal 310g of a user sniffling. The amplitude signal 310g may include one or more features 320g. For example, there may be intermittent features at approximately 3 seconds, 5 seconds, 7 seconds, 9 seconds, and 11 seconds.

In addition to the audio data plot 300g, FIG. 3G may include a processed audio data plot 350g. The processed audio data plot 350g may include one or more features 360g that may correspond to the one or more features 320g. For example, the feature 360g at approximately 9 seconds may correspond to the feature 320g of the amplitude signal 310g at approximately 9 seconds.

As illustrated in FIG. 3H the audio data plot 300h may include the amplitude signal 310h of a user yelling. The amplitude signal 310h may include one or more features 320h. For example, there may be intermittent features at approximately 6-8 seconds, 11-12 seconds, and 13-15 seconds.

In addition to the audio data plot 300h, FIG. 3H may include a processed audio data plot 350h. The processed audio data plot 350h may include one or more features 360h that may correspond to the one or more features 320h. For example, the feature 360h at approximately 11 seconds may correspond to the feature 320h of the amplitude signal 310h at approximately 11 seconds.

As illustrated in FIG. 3I the audio data plot 300i may include the amplitude signal 310i of a user laughing. The amplitude signal 310i may include one or more features 320i. For example, there may be intermittent features at approximately 3-6 seconds, 9 seconds, and 13 seconds.

In addition to the audio data plot 300i, FIG. 3I may include a processed audio data plot 350i. The processed audio data plot 350i may include one or more features 360i that may correspond to the one or more features 320i. For example, the feature 360i at approximately 9 seconds may correspond to the feature 320i of the amplitude signal 310i at approximately 9 seconds.

The examples of FIGS. 3A-3I are simply examples and it is appreciated that the present disclosure extends to other sound-producing behaviors such as wheezing, shortness of breath, sex, masturbation, etc. Additionally, the description related to FIG. 3A regarding feature extraction, frequency analysis, behavior identification, etc. are equally applicable to FIGS. 3B-3I.

Figure 4:
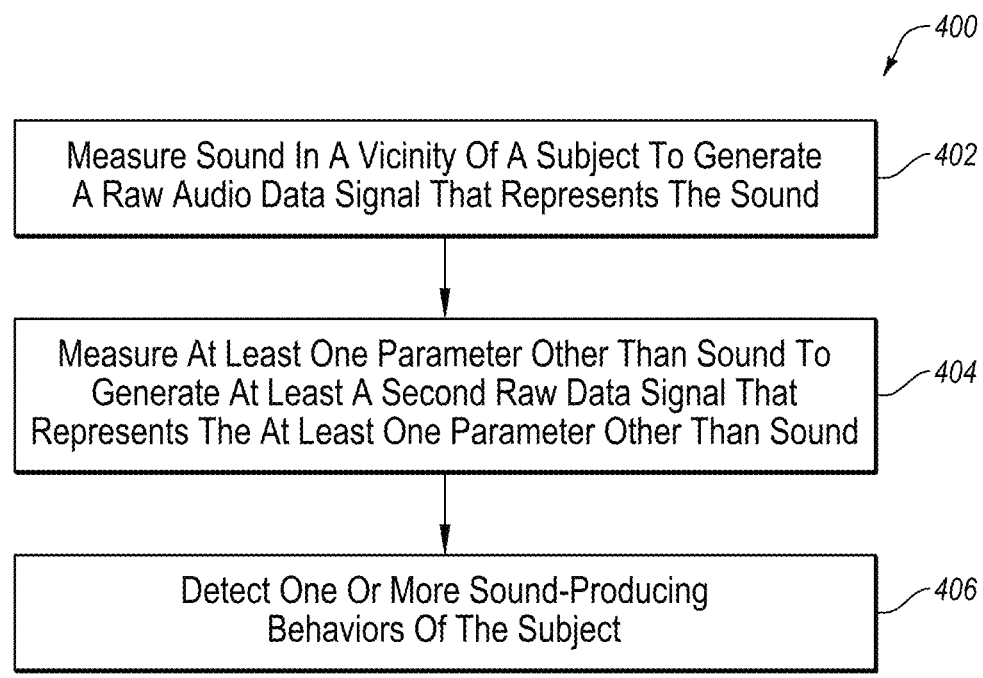
FIG. 4 includes a flow chart of an example method to measure sound-producing behaviors of a subject with a power- and bandwidth-limited electronic device that includes a processor.

FIG. 4 is a flowchart of an example method 400 to measure sound-producing behaviors of a subject with a power- and bandwidth-limited electronic device that includes a processor, arranged in accordance with at least one embodiment described herein. The method 400 may be implemented, in whole or in part, by the wearable electronic device 104, the smartphone 106, and/or the remote server 110 described elsewhere herein. Alternatively or additionally, execution of one or more of the feature extractor 210A and/or 210B, classifier 212A and/or 212B, annotation interface 214, and/or ML module 222 by the processor 202A and/or 202B of the wearable electronic device 104 and/or the remote server 110 may cause the corresponding processor 202A and/or 202B to perform or control performance of one or more of the operations or blocks of the method 400. The method 400 may include one or more of blocks 402, 404, and/or 406. The method 400 may begin at block 402.

At block 402, sound may be measured in a vicinity of a subject to generate an audio data signal that represents the sound. The sound may be measured by, e.g., a microphone communicatively coupled to the processor 202A of FIG. 2. The microphone may be included as one of the sensors 208 of the wearable electronic device 104 or as a discrete sensor or as a sensor integrated in a smartphone or other device apart from the wearable electronic device 104. The audio data signal may capture sounds the subject makes, such as coughing, sneezing, vomiting, shouting, talking, moving him/herself or other objects, opening closing doors, etc., as well as sounds made by others. Sound-producing behaviors of interest may generally each have a "signature" in the audio data signal, or recognizable aspects or patterns, that may be identified during feature extraction and/or classification to detect sound-producing behaviors. Block 402 may be followed by block 404.

At block 404, at least one parameter other than sound may be measured to generate at least a second data signal that represents the at least one parameter other than sound. The at least one parameter other than sound may be measured by a corresponding sensor communicatively coupled to the processor 202A of FIG. 2. For instance, an accelerometer communicatively coupled to the processor may measure acceleration of at least a portion of the subject to generate an acceleration data signal that represents acceleration of the at least the portion of the subject. As another example, a gyro sensor communicatively coupled to the processor may measure angular velocity of the at least the portion of the subject to generate an angular velocity data signal that represents angular velocity of the at least the portion of the subject. As another example, a PPG sensor communicatively coupled to the processor may measure blood flow of the subject to generate a blood flow data signal that represents blood flow of the subject. As another example, an ECG sensor communicatively coupled to the processor, electrical activity of a heart of the subject to generate an ECG data signal that represents electrical activity of the heart. As another example, an EDA sensor communicatively coupled to the processor may measure EDA of the subject to generate an EDA data signal that represents EDA of the subject.

Sound-producing behaviors and/or behaviors related thereto may generally have a signature in the corresponding data signal that may be identified during feature extraction and/or classification to detect sound-producing behaviors or the related behaviors. For example vomiting and/or shouting associated with rage (or mood) may be accompanied by an elevated heart rate that may be detected from the blood flow data signal and/or the ECG data signal and/or by changes in EDA that may be detected from the EDA data signal. As another example, sneezing and/or coughing may be accompanied by particular movements of the subject's arm or other body part (e.g., blood within a vessel) that may be detected from the acceleration data signal, the angular velocity data signal, and/or the blood flow data signal. Block 404 may be followed by block 406.

At block 406, one or more sound-producing behaviors of the subject may be detected based on: both the audio data signal and the second data signal (e.g., one or more of the acceleration data signal, the angular velocity data signal, the blood flow signal, the ECG signal, and/or the EDA signal); or information derived from both the audio data signal and the second data signal. The sound-producing behaviors may be detected by, e.g., the processor 202A of the wearable electronic device 104 and/or the processor 202B of the remote server 110 of FIG. 2.

The detecting may include detecting a sound-producing behavior at times when both the audio data signal and the second data signal or the information derived therefrom indicates a sound-producing behavior. Alternatively or additionally, the detecting may include extracting audio features from the audio data signal; extracting second features from the second data signal; classifying each audio feature of a first subset of the audio features and each feature of a first subset of the second features as indicative of a sound-producing behavior; and detecting the one or more sound-producing behaviors of the subject based on the classifying. The detecting may alternatively or additionally include recording each detected sound-producing behavior as such, including recording a time at which each sound-producing behavior occurred and/or other information about each sound-producing behavior. The detecting may further include sub-classifying or categorizing each audio feature of the first subset of audio features and each feature of the first subset of second features as indicative of a corresponding type of multiple different types of sound-producing behaviors (e.g., cough, sneeze, vomit, shouting)

Although not illustrated in FIG. 4, the method 400 may include one or more other operations instead of or in addition to those illustrated in FIG. 4. For instance, the method 400 may further include reporting information about sound-producing behaviors of the subject derived from one or both of the audio data signal or the second data signal to the remote server. For instance, one or more of the audio features extracted from the audio data signal may be reported to the remote server. Alternatively or additionally, one or more of the second features extracted from the second data signal may be reported to the remote server. Alternatively or additionally, one or more detected sound-producing behaviors and an occurrence time of each of the one or more detected sound-producing behaviors may be reported to the remote server. One or more of the foregoing may be reported to the remote server all without reporting to the remote server any of the audio data signal or any of the second data signal.

In some embodiments, the audio data signal and the second data signal may be time synchronized with each other. Alternatively or additionally, the audio features and the second features may be time synchronized with each other. In these and other embodiments, the detecting of sound-producing behaviors may include, for at least one of the sound-producing behaviors, determining that an audio feature of the first subset of audio features coincides chronologically with a second feature of the first subset of second features, each of the audio feature and the second feature being indicative of the sound-producing behavior.

Alternatively or additionally, where the audio data signal is relatively clean, sound-producing behaviors may be detected exclusively from the audio data signal without reference to the second data signal or where the audio data signal is very noisy, it may be discarded. For instance, the method 400 may include measuring sound in the vicinity of the subject within a subsequent period of time to generate a subsequent audio data signal that represents the sound. The method 400 may include extracting subsequent audio features from the subsequent audio data signal. The method 400 may include classifying each audio feature of a first subset of the subsequent audio features as indicative of a sound-producing behavior. The method 400 may include determining a quality score of the subsequent audio data signal. Additionally or alternatively, a quality score may be determined for other data signals. For example, for an audio data signal, the quality score may be based on amplitude peaks and frequencies that are consistent with what is expected for the particular user or for humans in general. As another example, for the audio data signal, the quality score may be based on a signal to noise ratio. As an additional example, for accelerometer data over a span of time, the quality score may be based on the shape of a curve of the acceleration data over the span of time, ratios in peaks/valleys of the acceleration data, frequency ranges of the acceleration data within typical ranges of human physiology, etc. In some embodiments, such a quality score may be determined based on initially obtained sensor data, such as initial audio data. Additionally or alternatively, the quality score may be determined based on processed data, such as a PSD of audio data. The method 400 may include one of the following. In response to determining that the quality score of the subsequent audio data signal exceeds a first threshold quality score, the method 400 may include detecting one or more sound-producing behaviors of the subject that occur within the subsequent period of time based exclusively on the first subset of the subsequent plurality of audio features without considering other data signals and/or features extracted from such other data signals. Alternatively, in response to determining that the quality score of the subsequent audio data signal is less than a second threshold quality score that is lower than the first threshold quality score, the method 400 may include discarding one or both of the subsequent audio data signal and the first subset of the subsequent audio features without detecting any sound-producing behaviors of the subject that occur within the subsequent period of time based thereon.

The method 400 may alternatively or additionally include receiving, from the subject, annotation input that may confirm, or not, the occurrence of one or more sound-producing behaviors. The annotations may be used to decrease measurement uncertainty in the data signals. For instance, if the annotations confirm that the subject sneezed, coughed, vomited, or shouted, this increases the certainty that a corresponding detected sneeze, cough, vomiting, or shout actually occurred. As another example, if the annotations indicate the subject did not actually sneeze, cough, vomit or shout despite the detection of such sound-generating behaviors by the wearable electronic device, this may indicate that the algorithms and/or state machines used in the detection of sound-producing behaviors are inaccurate and should be revised.

Some embodiments described herein may be applied across numerous subjects. In these and other embodiments, annotations may be requested from some or all of the subjects. For instance, annotations may be requested, e.g., by the wearable electronic device or by a smartphone or other user device, from only a certain percentage of subjects, from only those subjects that have opted in to providing annotations, or from all subjects. Alternatively or additionally, annotations may be requested from a given subject only infrequently, such as only once every X number of days, where X is an integer greater than 1. Alternatively or additionally, subjects may provide annotations as frequently as desired on their own rather than in response to a request for the annotations from the wearable electronic device.

The method 400 may alternatively or additionally include reporting annotations to the remote server. The annotations may be reported to the remote server by the wearable electronic device, or by a smartphone or other user device, that receives the annotations from the subject. The method 400 may include the remote server receiving the annotations and information about sound-producing behaviors from multiple subjects and updating one or more algorithms or state machines used in the detection (e.g., extraction and/or classifying) of sound-producing behaviors. The method 400 may also include the remote server sending one or more updated algorithms or state machines back down to the wearable electronic device for use in the future in the detection of sound-producing behaviors.

Figure 5:
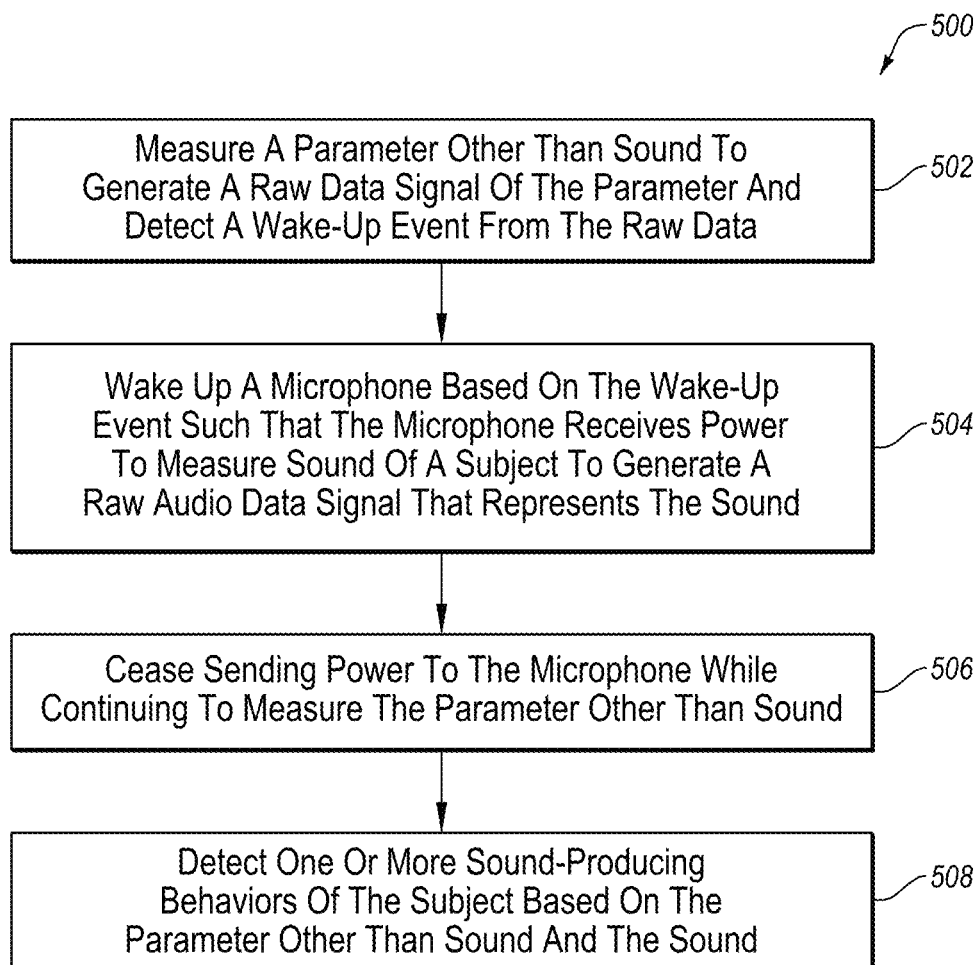
FIG. 5 includes a flow chart of another example method to measure sound-producing behaviors of a subject, all arranged in accordance with at least one embodiment described herein.

FIG. 5 is a flowchart of another example method 500 to measure sound-producing behaviors of a subject, arranged in accordance with at least one embodiment described herein. The method 500 may be implemented, in whole or in part, by the wearable electronic device 104, the smartphone 106, and/or the remote server 110 described elsewhere herein. Alternatively or additionally, execution of one or more of the feature extractor 210A and/or 210B, classifier 212A and/or 212B, annotation interface 214, and/or ML module 222 by the processor 202A and/or 202B of the wearable electronic device 104 and/or the remote server 110 may cause the corresponding processor 202A and/or 202B to perform or control performance of one or more of the operations or blocks of the method 500. The method 500 may include one or more of blocks 502, 504, 506, and/or 508. The method 500 may begin at block 502.

At block 502, at least one parameter other than sound may be measured to generate a data signal of the parameter and detect a wake-up event from the data. The at least one parameter other than sound may be measured by a corresponding sensor communicatively coupled to the processor 202A of FIG. 2. For instance, an accelerometer communicatively coupled to the processor may measure acceleration of at least a portion of the subject (e.g., the chest of the subject) to generate an acceleration data signal that represents acceleration of the at least the portion of the subject. As another example, a gyro sensor communicatively coupled to the processor may measure angular velocity of the at least the portion of the subject to generate an angular velocity data signal that represents angular velocity of the at least the portion of the subject. As another example, a PPG sensor communicatively coupled to the processor may measure blood flow of the subject to generate a blood flow data signal that represents blood flow of the subject. As another example, an ECG sensor communicatively coupled to the processor, electrical activity of a heart of the subject to generate an ECG data signal that represents electrical activity of the heart. As another example, an EDA sensor communicatively coupled to the processor may measure EDA of the subject to generate an EDA data signal that represents EDA of the subject.

In addition to generating the data signal, the data may be analyzed to determine whether or not a wake-up event has been detected within the data. For example, the data of an accelerometer may be analyzed to determine whether a sudden acceleration of the at least the portion of the subject (e.g., the chest of the subject) typical of a sneeze or cough has been detected. In some embodiments, a sensor measuring the parameter other than sound may continuously monitor for such a wake-up event. In these and other embodiments, the threshold of the wake-up event may be tuned to be more or less sensitive. For example, if a certain number of events is expected in a given twenty four hour period and less than the amount expected have occurred, the threshold may be lowered such that more wake-up events may be triggered. Additionally or alternatively, the threshold may be tuned based on which sound-producing behavior is being targeted. As another example, if another sensor (e.g., a temperature sensor) indicates that the subject is experiencing a fever or has an infection, the threshold of the wake-up event may be lowered such that more wake-up events are triggered. The block 502 may be followed by the block 504.

At block 504, a microphone may be woken up based on the wake-up event such that the microphone receives power to measure sound of a subject to generate an audio data signal that represents the sound. In some embodiments, the microphone may be woken up within one second (for example, between two hundred and five hundred milliseconds) of the wake-up event. The microphone may be communicatively coupled to the processor 202A of FIG. 2 such that the processor sends a signal to provide power to the microphone. Upon receiving power, the microphone may begin to capture audio data.

The microphone may be included as one of the sensors 208 of the wearable electronic device 104 or as a discrete sensor or as a sensor integrated in a smartphone or other device apart from the wearable electronic device 104. In some embodiments, the microphone may be oriented directly against the chest of the subject. The audio data signal may capture sounds the subject makes, such as coughing, sneezing, vomiting, shouting, talking, moving him/herself or other objects, opening closing doors, etc., as well as sounds made by others. The block 504 may be followed by the block 506.

At block 506, there may be a cessation of power being sent to the microphone, while the parameter other than sound may continue to be measured. In some embodiments, the processor 202A may be configured to continue to provide power to the microphone as long as the audio data signal appears to be associated with an event of interest, and after the audio data signal no longer appears to be associated with an event of interest, the processor may cease to provide the microphone power. Additionally or alternatively, the processor 202A may be configured to provide power to the microphone for a certain window of time (e.g., two seconds, four seconds, etc.) based on the wake-up event. In some embodiments, the processor 202A may provide power to the microphone based on a combination of the foregoing, for example, by providing power until the audio data signal no longer appears to be associated with an event of interest, after which the microphone may be provided with power to capture audio data for a certain window of time. In these and other embodiments, the sensor measuring the parameter other than sound may continue to monitor the parameter even if the microphone is not receiving power.

In some embodiments, the window of time may be based on a talking detection algorithm used on the audio data signal. For example, if talking is detected in the audio data, the window may be extended such that additional audio data may be collected. In these and other embodiments, processing may be performed on the extended window of audio data and the processed audio data may be retained and the unprocessed audio data may be discarded. In some embodiments, the lengthened window of time may provide additional data such that any words spoken in the audio data cannot be recreated, derived, or otherwise obtained from the processed audio data. For example, by including a longer segment the sample size of frequencies and/or powers is extended such that any single word is masked by the other words spoken or by other data collected. Doing so may protect the privacy of the subject and of others speaking when around the subject. If talking is not detected, the window may be kept to its normal length or even shortened, and the audio data may be retained or otherwise stored to be used for sound-producing behavior detection.

Sound-producing behaviors of interest may generally each have a "signature" in the audio data signal (including a frequency representation thereof), or recognizable aspects or patterns, that may be identified during feature extraction and/or classification to detect sound-producing behaviors. In some embodiments, such analyses may be performed on audio data, on processed audio data (e.g., the frequency domain of the audio data), etc.

Sound-producing behaviors and/or behaviors related thereto may generally have a signature in the corresponding data signal that may be identified during feature extraction and/or classification to detect sound-producing behaviors or the related behaviors. For example vomiting and/or shouting associated with rage (or mood) may be accompanied by an elevated heart rate that may be detected from the blood flow data signal and/or the ECG data signal and/or by changes in EDA that may be detected from the EDA data signal. As another example, sneezing and/or coughing may be accompanied by particular movements of the subject's chest or other body part (e.g., blood within a vessel) that may be detected from the acceleration data signal, the angular velocity data signal, and/or the blood flow data signal. Block 506 may be followed by block 508.

At block 508, one or more sound-producing behaviors of the subject may be detected based on both the parameter other than sound (e.g., one or more of the acceleration data signal, the angular velocity data signal, the blood flow signal, the ECG signal, and/or the EDA signal) and the sound; or information derived from both the audio data signal and the second data signal. The block 508 may be similar or comparable to the block 406 of FIG. 4.

Additionally, the method 500 may include any of the additional and not illustrated operations described above with reference to the method 400 of FIG. 4.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method to measure sound-producing behaviors of a subject with a power- and bandwidth-limited electronic device that includes a processor, the method comprising:
   measuring, by at least one sensor communicatively coupled to the processor, at least one parameter other than sound to generate a second data signal that represents the at least one parameter other than sound;
   detecting a wake-up event from the second data signal;
   providing power to a microphone communicatively coupled to the processor such that the microphone measures sound in a vicinity of the subject to generate an audio data signal that represents the sound;
   detecting one or more sound-producing behaviors of the subject based on:
      both the audio data signal and second data signal; or
      information derived from both the audio data signal and the second data signal, the detecting comprising:
         extracting, by the processor, a plurality of audio features from the audio data signal;
         extracting, by the processor, a plurality of second features from the second data signal;
         classifying each audio feature of a first subset of the plurality of audio features and each feature of a first subset of the plurality of second features as indicative of a sound-producing behavior; and
         detecting the one or more sound-producing behaviors of the subject based on the classifying; and
   measuring sound in the vicinity of the subject within a subsequent period of time to generate a subsequent audio data signal that represents the sound;
   extracting, by the processor, a subsequent plurality of audio features from the subsequent audio data signal;
   classifying each audio feature of a first subset of the subsequent plurality of audio features as indicative of a sound-producing behavior;
   determining a quality score of the subsequent audio data signal; and
   one of:
      in response to determining that the quality score of the subsequent audio data signal exceeds a first threshold quality score, detecting one or more sound-producing behaviors of the subject that occur within the subsequent period of time based exclusively on the first subset of the subsequent plurality of audio features; or
      in response to determining that the quality score of the subsequent audio data signal is less than a second threshold quality score that is lower than the first threshold quality score, discarding one or both of the subsequent audio data signal and the first subset of the subsequent plurality of audio features without detecting any sound-producing behaviors of the subject that occur within the subsequent period of time based thereon.

2. The method of claim 1, wherein measuring, by the at least one sensor, the at least one parameter other than sound to generate the second data signal comprises at least one of:
   measuring, by an accelerometer communicatively coupled to the processor, acceleration of a chest of the subject to generate an acceleration data signal that represents acceleration of the chest of the subject;
   measuring, by a gyro sensor communicatively coupled to the processor, angular velocity of at least a portion of the subject to generate an angular velocity data signal that represents angular velocity of the at least the portion of the subject;
   measuring, by a thermometer communicatively coupled to the processor, at least one of a skin temperature or a core body temperature of the subject to generate a temperature signal that represents at least one of the skin temperature or the core body temperature of the subject;

measuring, by an oxygen saturation sensor communicatively coupled to the processor, blood oxygenation of the subject to generate an oxygen saturation signal of the oxygen saturation level of the subject;

measuring, by a photoplethysmograph (PPG) sensor communicatively coupled to the processor, blood flow of the subject to generate a blood flow data signal that represents blood flow of the subject;

measuring, by an electrocardiograph (ECG) sensor communicatively coupled to the processor, electrical activity of a heart of the subject to generate an ECG data signal that represents electrical activity of the heart; or measuring, by an electrodermal activity (EDA) sensor communicatively coupled to the processor, EDA of the subject to generate an EDA data signal that represents EDA of the subject.

3. The method of claim 1, wherein the detecting further includes sub-classifying each audio feature of the first subset of the plurality of audio features and each feature of the first subset of the plurality of second features as indicative of a corresponding type of multiple different types of sound-producing behaviors.

4. The method of claim 3, wherein the different types of sound-producing behaviors include at least one of sneezing, wheezing, shortness of breath, chewing, swallowing, masturbation, sex, coughing, vomiting, and shouting.

5. The method of claim 1, further comprising reporting to a remote server information about sound-producing behaviors of the subject derived from one or both of the audio data signal or the second data signal.

6. The method of claim 5, wherein the reporting to the remote server includes at least one of:

reporting to the remote server one or more of the plurality of audio features extracted from the audio data signal;

reporting to the remote server one or more of the plurality of second features extracted from the second data signal; or reporting to the remote server one or more detected sound-producing behaviors and an occurrence time of each of the one or more detected sound-producing behaviors, all without reporting to the remote server any of the audio data signal or any of the second data signal.

7. The method of claim 1, further comprising:

receiving from the subject annotation input that confirms occurrence of one or more sound-producing behaviors;

reporting, to a remote server, the annotation input, wherein the remote server is configured to receive annotation inputs and information about sound-producing behaviors from a plurality of subjects and to update an algorithm used in the classifying; and receiving, from the remote server, the updated algorithm.

* * * * *